US009029415B2

(12) United States Patent
Küper et al.

(10) Patent No.: US 9,029,415 B2
(45) Date of Patent: May 12, 2015

(54) COOLING MIXTURES WITH AN ENHANCED COOLING EFFECT OF 5-METHYL-2-(PROPANE-2-YL)CYCLOHEXYL-N-ETHYLOXAMATE

(75) Inventors: Thomas Küper, Reken (DE); Heiko Oertling, Holzminden (DE); Sabine Lange, Holzminden (DE)

(73) Assignee: Symrise AG, Holzminden (DE)

( * ) Notice: Subject to any disclaimer, the term of this patent is extended or adjusted under 35 U.S.C. 154(b) by 56 days.

(21) Appl. No.: 13/159,925

(22) Filed: Jun. 14, 2011

(65) Prior Publication Data

US 2011/0305657 A1 Dec. 15, 2011

Related U.S. Application Data

(60) Provisional application No. 61/354,484, filed on Jun. 14, 2010.

(51) Int. Cl.
*A61K 31/215* (2006.01)
*A61K 8/44* (2006.01)
*A61Q 5/00* (2006.01)
*A61Q 19/00* (2006.01)

(52) U.S. Cl.
CPC ............. *A61K 8/44* (2013.01); *A61K 2800/244* (2013.01); *A61Q 5/00* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 2,973,282 A | 2/1961 | Gross | |
| 3,307,544 A | 3/1967 | Gander et al. | |
| 4,262,003 A | 4/1981 | Urquhart et al. | |
| 6,893,626 B2 | 5/2005 | Wei | |
| 2003/0207904 A1 | 11/2003 | Wei | |
| 2004/0028714 A1 | 2/2004 | Blondeau et al. | |
| 2004/0082928 A1* | 4/2004 | Pesce et al. | 604/361 |
| 2009/0054520 A1* | 2/2009 | Surburg et al. | 514/529 |
| 2011/0117147 A1* | 5/2011 | Ishida et al. | 424/401 |

FOREIGN PATENT DOCUMENTS

| | | | | |
|---|---|---|---|---|
| DE | 10055940 A1 | 5/2002 | | |
| EP | 0186071 A2 | 7/1986 | | |
| EP | 2033668 A2 | 3/2009 | | |
| GB | 1315761 A | 5/1973 | | |
| GB | 1351761 A | 5/1974 | | |
| WO | 3807283 A1 | 9/1989 | | |
| WO | WO-0215692 A1 | 2/2002 | | |
| WO | WO-0238537 A1 | 5/2002 | | |
| WO | WO-04000023 A1 | 12/2003 | | |
| WO | WO-2004/026840 A1 | 4/2004 | | |
| WO | WO2006069953 | * | 7/2006 | ............... A61K 8/34 |
| WO | WO-2007019719 A1 | 2/2007 | | |

OTHER PUBLICATIONS

Clapham, D.E., et al., "International Union of Pharmacology. XLIX, Nomenclature and Structure-Function Relationships of Transient Receptor Potential Channels," 2005, *Pharmacological Reviews*, 57 (4), 427-450.
Peier, A.M., et al., "A TRP Channel that Senses Cold Stimuli and Menthol," 2005, *Cell*, 108 (5), 705-15.
Watson, H.R., et al., "New compounds with the menthol cooling effect," *J. Soc. Cosmet. Chem.* 29, 1978, 185-200.
Furrer, S.M., et al., "New Developments in the Chemistry of Cooling Compounds," Chem. Percept. 1, 2008, 119-126.
Wei, E.T., et al., "AG-3-5: a chemical producing sensations of cold," J. Pharm. Pharmacol. 35, 1983, 110-112.
Beck, B., et al., "Prospects for prostate cancer imaging and therapy using high-affinity TRPM8 activators," Cell Calcium, 41, 2007, 285-294.
Levine, J.D., et al., "TRP channels: Targets for the relief of pain," Biochim. Biophys. Acta, 1772, 2007. 989-1003.
Mukerji, G., et al., "Cool and methol receptor TRPM8 in human urinary bladder disorders and clinical correlations," *BMC Urology* 6, 2006, 1-11.
Lashinger, E.S.R., et al., "AMTB, a TRPM8 channel blocker: evidence in rats for activity in overactive bladder and painful bladder syndrome," Am. J. Physiol. Renal Physiol. 295, 2008, 303-310.
Slominski, A., "*Cooling skin cancer: menthol inhibits melanoma growth*. Focus on TRPM8 activiation suppresses cellular viability in human melanoma," Am. J. Physiol. 295, 2008, 293-295.
Yamamura, H., et al., "TRPM8 activiation suppresses cellular viability in human melanoma," *Am J. Physiol Cell Physiol.* 295, 2008, 296-301.
Wasner, G., et al., "Topical menthol-a human model for cold pain by activiation and sensitization of C nociceptors," *Brain*, 2004, 127, 1159-1171.
Green, B.G., et al., "Thermal and nociceptive sensations from menthol and their suppression by dynamic contact," *Behavioural Brain Research*, 2007, 176, 284-291.
Monkhouse, D.C., et al., "Transdermal Drug Delivery," Drug Development and industrial Pharmacy, 14 (2&3), (1988), 183-209.
Chien, Y.W., "Development of Transdermal Drug Delivery Systems," Drug Development and Industrial Pharmacy, 13(4&5), 589-651, (1987).
Chien, Y.W., "Transdermal Rate-Controlled Drug Delivery: Theory and Practice," Drugs of Today, vol. 23, No. 1, 1987, 625-646.

* cited by examiner

*Primary Examiner* — Hasan Ahmed
(74) *Attorney, Agent, or Firm* — Dilworth & Barrese, LLP

(57) ABSTRACT

The invention relates to a cooling mixture comprising or consisting of 5-methyl-2-(propane-2-yl)cyclohexyl-N-ethyloxamate and one, two, three or more certain polyols. It further relates to a cosmetic composition comprising such a cooling mixture or to a sanitary article comprising such a cooling mixture. The invention also relates to the use of certain polyols for enhancing the cooling effect of 5-methyl-2-(propane-2-yl)cyclohexyl-N-ethyloxamate on the skin or a mucous membrane, a method for generating an enhanced cooling effect of 5-methyl-2-(propane-2-yl)cyclohexyl-N-ethyloxamate on the skin or a mucous membrane as well as a method for generating a corresponding cooling mixture.

12 Claims, 1 Drawing Sheet

COOLING MIXTURES WITH AN ENHANCED COOLING EFFECT OF 5-METHYL-2-(PROPANE-2-YL)CYCLOHEXYL-N-ETHYLOXAMATE

CROSS-REFERENCE TO RELATED APPLICATIONS

This application claims priority to Provisional Patent Application No. 61/354,484, filed in the United States on Jun. 14, 2010, the entire contents of which is incorporated herein by reference.

The invention relates to a cooling mixture comprising or consisting of 5-methyl-2-(propane-2-yl)cyclohexyl-N-ethyloxamate and one, two, three or more certain polyols. It further relates to a cosmetic composition comprising such a cooling mixture or a sanitary article comprising such a cooling mixture. Moreover, the invention relates to the use of certain polyols for enhancing the cooling effect of 5-methyl-2-(propane-2-yl)cyclohexyl-N-ethyloxamate on the skin or a mucous membrane, a method for generating an enhanced cooling effect of 5-methyl-2-(propane-2-yl)cyclohexyl-N-ethyloxamate on the skin or a mucous membrane as well as a method for producing a corresponding cooling mixture.

BACKGROUND OF THE INVENTION

Cooling substances are used in the area of personal care for application onto the skin, hair and mucous membranes. Such applications include lotions and creams, skin cleansers, shampoos, hair conditioners, cleaning tissues, sanitary towels, tampons, nappies as well as other cosmetic products such as lipsticks or Eau de Toilette. A multiplicity of cooling substances of natural and synthetic origin has been described. The most well known substance out of these is menthol, in particular l-menthol, which was initially found in peppermint oil. Menthol binds to the TRPM8 (Transient Receptor Potential Melastatin 8) receptor also known under the designation of CMR (Cold Menthol Receptor 1). This receptor belongs to the family of TRPs (Transient Receptor Potential Ion Channels) and is expressed in specific peripheral neurons, where it forms a pore consisting of four protein monomers. Low temperatures as well as the binding of cooling substances to the channel will open the latter and will thus allow calcium and sodium ions to enter through the membrane. This flow of ions results in a depolarization of the membrane and a generation of an action potential which will be converted in the brain into a sensation of cold (Clapham D E et al 2005, *Pharmacological reviews*, 57 (4), 427-450; Peier A M et al 2005, *Cell*, 108 (5), 705-15). Several menthol derivatives have been described, which induced the opening of TRPM8 (British Patent 1971 #1315761 Watson H. R., *J. Soc. Cosmet. Chem.* 29, 1978, 185-200; Furrer S. M., *Chem. Percept.* 1, 2008, 119-126), however, there are also structures which have a cooling effect and are not based on menthol, such as Icilin (Wei E. T., *J. Pharm. Pharmacol.* 35, 1983, 110-112; WO 2004/026840), WS-23 or substances such as mentioned in WO 2007/019719.

Activators of TRPM8 may have an repellent effect on insects (WO 2002/015692, WO 2004/000023, US 2004/0028714) and may also have calming properties during the treatment of inflammation-induced pain and hyperalgesia as well as a hyperactive bladder (Beck B. *Cell Calcium*, 41, 2007, 285-294; Levine J. D. *Biochim. Biophys. Acta. Mol. Basis. Dis.* 1772, 2007, 989-1003; Mukerji G., *BMC Urology* 6, 2006, 6; US 2003/0207904; US 2005/6893626, Lashinger E S. *Am. J. Physiol. Renal Physiol.* 295, 2008, 303-810).

A number of studies could further show that some activators of TRPM8 have a growth inhibiting effect on tumors (Slominski A., *Am. J. Physiol.* 295, 2008, 293-295; Yamamura H, *Am. J. Physiol. Cell Physiol.* 295, 2008, 296-301).

Due to their close structural relationship to menthol, many cooling substances have an odor similar to that of mint and are therefore not suitable for topical application. In addition, a high concentration of more than 3% has to be used in many physiological cooling substances, in order to induce a tangible cooling effect. High concentrations of cooling substances may cause undesired side effects such as stinging and burning on the skin (Wasner G., *Brain*, 2004, 127, 1159-1171; Green B G, *Behav Brain Res*, 2007, 176, 284-291).

In the light of this background it is the object of the present invention to provide a combination of active substances which enables the use of a suitable active cooling substance for topical applications at a reduced concentration.

This object is achieved by means of a cooling mixture comprising or consisting of:
(a) 5-methyl-2-(propane-2-yl)cyclohexyl-N-ethyloxamate (Formula I)

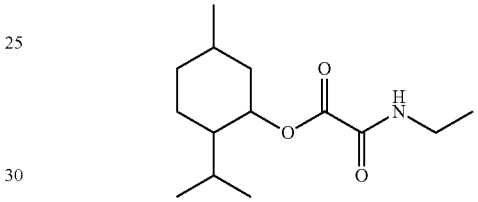

and
(b) one, two, three or more polyols selected from group A consisting of branched or unbranched alkanediols and branched or unbranched alkanetriols each having 3-12 carbon atoms.

5-Methyl-2-(propane-2-yl)cyclohexyl-N-ethyloxamate is known from EP 2 033 688 A2 as an active cooling substance. Surprisingly, the inventors have now been able to show that the combination of these compounds with branched or unbranched alkanedioles or branched or unbranched alkanetrioles each having 3 to 12 carbon atoms results in an enhancement of the cooling effect in the case of a topical application. This is not an additive effect since the corresponding diols and triols do not possess a cooling effect.

A cooling mixture in terms of the present invention comprises herein a sufficient amount of 5-methyl-2-(propane-2-yl)cyclohexyl-N-ethyloxamate, so that a cooling effect will be perceived in the case of a topical application. Preferably, a corresponding cooling mixture comprises a sufficient amount of 5-methyl-2-(propane-2-yl)cyclohexyl-N-ethyloxamate, so that a cooling effect would be perceived in the case of a topical application even if the concentration of all of the other active cooling substances was 0. Of course it is possible within the scope of the invention that the cooling mixture comprises an amount of 5-methyl-2-(propane-2-yl)cyclohexyl-N-ethyloxamate which is so low that this may be perceived only as a result of an enhancement by the corresponding polyols.

In case of doubt, the perceptibility of the cooling effect is to be determined by means of a panel test wherein the corresponding mixture is applied onto the skin of at least 10 test persons. If in the course of this, preferably in combination with a blind test, 90% of the test persons confirm a cooling effect, then this will preferably correspond to the criteria for the presence of a corresponding effect. Topical applications in terms of the present text are applications where the corresponding active substance or the combination of active substances is brought into contact with the skin or with a mucous membrane.

Preferred is a cooling mixture according to the invention, wherein at least part of the 5-methyl-2-(propane-2-yl)cyclohexyl-N-ethyloxamate is present in the (1R,2S,5R) configuration (formula II):

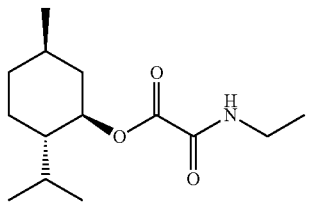 [SMILES: CCNC(=O)C(=O)O[C@@H]1C[C@H](C)CC[C@H]1C(C)C]

The 1R,2S,5R isomer of 5-methyl-2-(propane-2-yl)cyclohexyl-N-ethyloxamate is particularly accessible for an enhancement of the cooling effect and may in addition by synthesized in an economical manner via L-menthol as a starting compound.

Correspondingly, a cooling mixture according to the invention is preferred, wherein the proportion of 5-methyl-2-(propan-2-yl)cyclohexyl-N-ethyloxamate present in the (1R,2S, 5R) configuration in relation to the overall proportion of 5-methyl-2-(propane-2-yl)cyclohexyl-N-ethyloxamate is 45%, preferably 70% and particularly probably 97%.

According to the invention, as an alternative or in addition to the preferred embodiments, a cooling mixture according to the invention is preferred, wherein the ratio between the amount of substance of 5-methyl-2-(propane-2-yl)cyclohexyl-N-ethyloxamate and the amount of substance of the polyol or of the polyols of group A taken together is 1:20 to 1:0.1, preferably 1:10 to 1:1:0.5 [sic] and particularly preferably 1:5 to 1:1.

In terms of the invention it is further preferred if in the cooling mixture according to the invention, a or the polyol or several or all of the polyols of group A is or are selected from the group consisting of branched or unbranched alkanediols having 3 to 12 carbon atoms.

It is further preferred for the cooling mixture according to the invention, if in a or the alkanepolyol of group A or in several or all of the alkanepolyols of group A both or at least two of the hydroxyl groups are positioned vicinal to one another.

In addition, a cooling mixture according to the invention is preferred wherein exclusively one or more branched or unbranched 1,2-alkanediols having 5 to 12 carbon atoms are used as component (b).

The last-mentioned preferred variants of the cooling mixture each result, either alone or in a combination of the preferred features, in an improved enhancing effect for the actual active cooling substance 5-methyl-2-(propane-2-yl)cyclohexyl-N-ethyloxamate. Preferred diols or triols for the cooling mixture as component (b) [sic] part of component (b) are 1,2-pentanediol, 1,2-hexanediol, 1,2-heptanediol, 1,2-octanediol, 1,2-nonanediol, 1,2-decanediol, 1,2-dodecanediol and glycerol.

What is particularly preferred in this context is that component (b) in the cooling mixture comprises or consists of n-1,2-pentanediol.

Provided the cooling mixture according to the invention comprises n-1,2-pentanediol, it is preferred if the ratio between the amount of substance of 5-methyl-2-(propane-2-yl)cyclohexy-N-ethyloxamate and the amount of substance of n-1,2-pentanediol is 1:20 to 1:0.1, preferably 1:10 to 1:0.5 and particularly preferably 1:5 to 1:1.

In the case of this quantity ratio of substances, n-1,2-pentanediol (also as pentylene glycol) will develop its enhancing effect especially well. Moreover, corresponding ratios are to be regarded as especially economical with regard to their cost-benefit factor.

Further preferred is a cooling mixture according to the invention, which as a further component comprises a compound having an antagonistic effect on the heat receptors of the skin or of mucous membranes and thus reduces the sensation of heat. Trans-4-tert.-butylcyclohexanol is preferably used as such a compound.

Preferably, these compounds, and in particular trans-4-tert.-butylcyclohexanol, are used in a quantity ratio of substances relative to the sum of diols and triols of 100:1 to 1:1000, more preferably of 10:1 to 1:100 and particularly preferably of 1:1 to 1:10.

By adding corresponding heat receptor antagonists it is possible to enhance the perceived cooling effect mediated via cooling receptors subjectively even further by reducing the sensitivity of the heat receptors.

Part of the invention is also a cosmetic composition comprising a cooling mixture according to the invention.

Also part of the invention is a sanitary article comprising a cooling mixture according to the invention.

Preferred cosmetic compositions are hair care products and skin care products, preferred sanitary articles are sanitary towels, tampons and nappies, in particular baby nappies.

For cosmetic compositions it is preferred if the proportion of 5-methyl-2-(propane-2-yl)cyclohexyl-N-ethyloxamate in the overall composition is in the range of 0.001 to 20, preferably of 0.01 to 10 and especially of 0.1 to 5% by wt. respectively in relation to the overall weight of the cosmetic composition.

For sanitary articles it is preferred if the proportion of 5-methyl-2-(propane-2-yl)cyclohexyl-N-ethyloxamate in the overall composition is in the range of 0.000001 to 20, preferably of 0.0001 to 10 and especially of 0.001 to 5% by wt. respectively in relation to the overall weight of the sanitary article.

Cooling Skin and Hair Care Products

According to a preferred embodiment, the compositions according to the invention are a cooling skin or hair care product or cleansing agent.

Preferred skin or hair cleansing compositions are soaps having a liquid to gel type consistency, in particular transparent soaps, luxurious soaps, deodorant soaps, cream soaps, baby soaps, skin protection soaps, abrasive soaps and syndets, pasty soaps, soft soaps, washing pastes, peeling soaps, liquid wash, shower and bath preparations such as wash lotions, shower baths and shower gels, foam baths, oil baths and scrub preparations, shaving foams, lotions and creams.

According to a further preferred embodiment this is a shower gel, a shampoo formulation or a bath preparation. Such compositions according to the invention contain at least one cooling mixture according to the invention as well as usually anionic surfactants as primary surfactants and amphoteric and/or non-ionic surfactants as co-surfactants. Further suitable active substances and/or auxiliary agents are generally selected from lipids, perfume oils, colorants, organic acids, preservatives and antioxidants as well as from thickeners/gel formers, skin conditioners and moisture retainers.

i) Special Embodiments for Compositions According to the Invention for Application onto the Skin (Skin Care Products):

Suitable skin cosmetic compositions are for example toners, face masks, deodorants and other cosmetic lotions, compositions for the use in decorative cosmetics comprise for example blemish sticks, studio pigments, mascara and eye shadows, lipsticks, eye liner pens, eyeliner, rouges, powder and eyebrow pencils.

Moreover, the compositions according to the invention may be used in nose strips for pore cleaning, in anti-acne products, repellents, shaving products, after- and pre-shave care products, after-sun care products, hair removing agents, hand cleaning products, hair dyes, intimate hygiene products, foot care products as well as in baby care products.

The skin care products according to the invention are preferably W/O or O/W skin creams, day and night creams, eye creams, face creams, anti wrinkle creams, sun protection creams, moisture retention creams, bleaching creams, self-tanning creams, vitamin creams, skin lotions, care lotions and moisture retention lotions.

Depending on the area of application, the compositions according to the invention may be applied in a form suitable for skin care, such as for example as a cream, foam, gel, stick, mousse, milk, spray (pump spray or a spray containing a blowing agent) or as a lotion.

Apart from the cooling mixtures according to the invention and suitable carriers, the compositions according to the invention may contain also further active substances and auxiliary agents that are in customary use in skin cosmetics, in particular as described above. These include preferably emulsifiers, preservatives, perfume oils, active cosmetic substances such as phytantriol, vitamins A, E and C, retinol, bisabolol, panthenol, sun screen compositions, bleaching products, dyestuffs, toning agents, tanning agents, collagen, enzymes, protein hydrolysate, stabilizing agents, pH regulators, dyestuffs, salts, thickeners, gel formers, consistency agents, silicones, moisture retaining agents, re-moisturizing agents and further customary additives.

Preferred oil and fat components of the skin cosmetic compositions according to the invention are the above-mentioned mineral and synthetic oils such as for example paraffins, silicone oils and aliphatic hydrocarbons having more than 8 carbon atoms, animal and vegetable oils such as for example sunflower oil, coconut oil, avocado oil, olive oil, lanolin or waxes, fatty acids, fatty acid esters such as for example triglycerides of $C_6$-$C_{30}$ fatty acids, wax ester such as for example jojoba oil, fatty alcohols, vaseline, hydrogenated lanolin and acetylated lanolin as well as mixtures thereof.

In order to achieve certain properties such as an improved feel to touch, spreading, water resistance and/or binding of active substances and auxiliary agents, such as for example pigments, the skin cosmetic compositions according to the invention may additionally also contain conditioning substances on the basis of silicone compounds. Suitable silicone compounds are in particular polyalkyl siloxanes, polyaryl siloxanes, polyarylalkyl siloxanes, polyether siloxanes or silicone resins.

The preparation of the cosmetic compositions according to the invention is carried out according to customary methods as known by a person skilled in the art.

For the preparation of the compositions according to the invention, the active substances may be mixed or diluted with a suitable auxiliary agent (excipient). Excipients may be solid, semi-solid or liquid materials which may be used as a vehicle, carrier or medium for the active substances. The admixture of further auxiliary agents may, if desired, be carried out in a manner known to a person skilled in the art. In addition, polymers and dispersions are suitable, as auxiliary agents in pharmacy, preferably as or in (a) coating agent(s) or as (a) binder(s) for solid dosage forms. They may also be used as tablet coating agents and tablet binding agents.

Preferably, the cosmetic compositions according to the invention are present in the form of emulsions, in particular as water-in-oil (W/O) or oil-in-water (O/W) emulsions. However, it is also possible to select other types of formulations, for example gels, oils, oleogels, multiple emulsions, for example in the form of W/O/W or O/W/0 emulsionen, anhydrous ointments or ointment bases etc. Also emulsifier-free formulations such as hydrodispersions, hydrogels or a Pickering emulsion are advantageous embodiments.

The preparation of emulsions is carried out according to known methods. Apart from at least one active substance according to the invention, the emulsions contain as a rule usual components such as fatty alcohols, fatty acid esters and in particular fatty acid triglycerides, fatty acids, lanolin and derivatives thereof, natural or synthetic oils or waxes and emulsifiers in the presence of water. The selection of emulsion type specific additives and the preparation of suitable emulsions are described, for example, in Schrader, Grundlagen and Rezepturen der Kosmetika, Hüthig Buch Verlag, Heidelberg, $2^{nd}$ edition, 1989, part three, to which reference is herewith explicitly made.

A suitable emulsion as a W/O emulsion, for example for a skin cream etc. generally includes an aqueous phase which is emulsified by means of a suitable emulsifier system in an oil or fat phase. A polyelectrolyte complex is used for providing the aqueous phase.

Preferred fatty components which may be included in the fat phase of the emulsions are: hydrocarbon oils such as paraffin oil, purcellin oil, perhydrosqualene and solutions of microcrystalline waxes in these oils; animal or vegetable oils such as sweet almond oil, avocado oil, calophyllum oil, lanolin and derivates thereof, castor oil, sesame oil, olive oil, jojoba oil, Karite oil, hoplostethus oil, mineral oils having a distillation starting point under atmospheric pressure at approx. 250° C. and a distillation end point at 410° C., such as for example vaseline oil, esters of saturated or unsaturated fatty acids such as alkyl myristate, e.g. i-propyl, butyl or cetyl myristate, hexadecyl stearate, ethyl or i-propyl palmitate, octane or decanoic acid triglyceride and cetyl ricinoleate.

The fat phase may contain soluble silicone oils such as dimethyl polysiloxan, methylphenyl polysiloxane and the silicone glycol copolymer, fatty acids and fatty alcohols also in other oils.

Besides the cooling mixtures according to the invention also waxes may be used, such as for example carnauba wax, candililla wax, beeswax, microcrystalline wax, Ozokerit wax and Ca, Mg and Al oleates, myristates, linoleates and stearates.

Further, a composition according to the invention may be present as an O/W emulsion. Such an emulsion usually contains an oil phase, emulsifiers which stabilize the oil phase in the water phase, and an aqueous phase which is usually present in a thickened condition. As emulsifiers, O/W emulsifiers such as polyglycerin ester, sorbitan ester or partially esterified glycerides are considered.

According to a further preferred embodiment, the compositions according to the invention may be a shower gel, a shampoo formulation or a bath preparation.

Such formulations contain at least one cooling mixture according to the invention as well as usually anionic surfactants as primary surfactants and amphoteric and/or non-ionic surfactants as co-surfactants. Further suitable active substances and/or auxiliary agents are generally selected from lipids, perfume oils, dyestuffs, organic acids, preservatives and antioxidants as well as from thickeners/gel formers, skin conditioners and moisture retention agents.

In the wash, shower and bath compositions according to the invention, all of the anionic, neutral, amphoteric or cationic surfactants that are usually used in body cleansing agents may be used.

Suitable anionic surfactants are for example alkyl sulfates, alkyl ether sulfates, alkyl sulfonates, alkyl aryl sulfonates, alkyl succinates, alkyl sulfosuccinates, N-alkoyl sarcosinates, acyl taurates, acyl isothionates, alkyl phosphates, alkyl ether phosphates, alkyl ether carboxylates, alpha-olefin sulfonates, in particular alkaline and earth alkaline metal salts, e.g. sodium, potassium, magnesium, calcium as well as ammonium and triethanolamine salts. The alkyl ether sulfates, alkyl ether phosphates and alkyl ether carboxylates may contain 1 to 10 ethylene oxide or propylene oxide units, preferably 1 to 3 ethylene oxide units in a molecule.

These include e.g. sodium lauryl sulfate, ammonium lauryl sulfate, sodium lauryl ether sulfate, ammonium lauryl ether sulfate, sodium lauryl sarcosinate, sodium oleyl succinate, ammonium lauryl sulfosuccinate, sodium dodecyl benzol sulfonate, triethanolamine dodecyl benzol sulfonate.

Suitable amphoteric surfactants are for example alkyl betaine, alkyl amido propyle betaine, alkyl sulfobetaine, alkyl glycinate, alkyl carboxy glycinates, alkyl amphoacetates or propionates, alkyl amphodiacetates or dipropionates.

For example, coco dimethyl sulfopropyl betaine, lauryl betaine, cocamido propyl betaine or sodium cocoamphopropionate may be used.

As non-ionic surfactants for example the reaction products of aliphatic alcohols or alkyl phenols having 6 to 20 C atoms in the alkyl chain, which may be linear or branched, with ethylene oxide and/or propylene oxide are suitable. The amount of alkylene oxide is approx. 6 to 60 moles per mole of alcohol. Further, alkyl amine oxides, mono- or dialkyl alkanolamides, fatty acid esters of polyethylene glykolen, ethoxylated fatty acid amides, alkyl polyglycosides or sorbitan ether ester are suitable.

Moreover, the wash, shower and bath compositions according to the invention may contain usual cationic surfactants such as for example quaternary ammonium compounds, for example cetyl trimethyl ammonium chloride.

Further, the shower gel/shampoo formulations may contain a thickener such as e.g. common salt, PEG-55, propylene glycol oleate, PEG-120 methyl lucose ioleate and others as well as preservatives, further active substances and auxiliary agents and water.

Cosmetic compositions according to the invention in terms of a skin care product may also be sun protection compositions. It will be clear to a person skilled in the art that sun protection compositions may also be use for purposes other than skin care. In terms of the present application, however, sun protection compositions are understood to be skin care products (in the broadest possible sense). Sun protection compositions according to the invention comprise a cooling mixture according to the invention.

Advantageously, these compositions contain at least one UVA filter and/or at least one UVB filter and/or at least one anorganic pigment. The composition may here be present in different forms, such as are usually used for example for sun protection compositions. Thus, they may form for example a solution, an emulsion of the water-in-oil (W/O) or of the oil-in-water (O/W) type, or a multiple emulsion, for example of the water-in-oil-in-water (W/O/W) type, a gel, a hdrodispersion, a solid stick or an aerosol.

The sun protection compositions according to the invention may particularly advantageously be combined with substances which absorb or reflect UV radiation, wherein the overall amount of the filter substances is 0.01% by wt. to 40% by wt., preferably 0.1% to 10% by wt., in particular 1.0 to 5.0% by wt. in relation to the overall weight of the compositions, in order to provide cosmetic compositions which protect the hair or the skin from ultraviolet radiation. Advantageously, these compositions contain at least one UVA filter and/or at least one UVB filter and/or at least one anorganic pigment, so that a sun protection factor of at least 2 (preferably 5) is achieved. These compositions according to the invention may be present here in different forms as are customarily used for example for sun protection compositions. Thus, they may constitute for example a solution, an emulsion of the water-in-oil (W/O) type or of the oil-in-water (O/W) type or a multiple emulsion, for example of the water-in-oil-in-water (W/O/W) type, a gel, a hydrodispersion, a solid stick or an aerosol.

Advantageous UV filters are
UVB filters such as for example:
  p-aminobenzoic acid
  p-aminobenzoic acid ethyl ester (25 mole) ethoxylated
  p-dimethyl aminobenzoic acid-2-ethyl hexyl ester
  p-aminobenzoic acid ethyl ester (2 mole) N-propoxylated
  p-aminobenzoic acid glycerine ester
  salicylic acid homomethyl ester (homosalate) (Neo Heliopan®HMS)
  salicylic acid-2-ethyl hexyl ester (Neo Heliopan®OS)
  triethanol amino salicylate
  4-isopropyl benzyl salicylate
  anthranilic acid menthyl ester (Neo Heliopan®MA)
  diisopropyl cinnamic acid ethyl ester
  p-methoxy cinnamic acid-2-ethyl hexyl ester (Neo Heliopan®AV)
  diisopropyl cinnamic acid methyl ester
  p-methoxy cinnamic acid isoamyl ester (Neo Heliopan®E 1000)
  p-methoxy cinnamic acid diethanol amine salt
  p-methoxy cinnamic acid isopropyl ester
  2-phenyl benzimidazol sulfonic acid and salts (Neo Heliopan®Hydro)
  3-(4'-trimethyl ammonium)-benzyliden-bornan-2-one-methyl sulfate
  β-imidazol-4(5)-acrylic acid (urocanic acid)
  3-(4'-sulfo)benzyliden-bornan-2-one and salts
  3-(4'-methyl benzylidene)-d,l-camphor (Neo Heliopan®MBC)
  3-benzylidene-d,l-camphor
  N-[(2 and 4)-[2-(oxoborn-3-ylidene)methyl]benzyl]-acrylamide polymer
  4,4'-[(6-[4-(1,1-dimethyl)-aminocarbonyl)-phenylamino]-1,3,5-triazin-2,4-diyl)diimino]-bis-(benzoic acid-2-ethyl hexyl ester) (Uvasorb®HEB)
  benzylidene malonate polysiloxan (Parsol®SLX)
  glyceryl ethyl hexanoate dimethoxy cinnamate
  dipropylene glycol salicylate
  tris(2-ethylhexyl)-4,4",4"-(1,35-triazin-2,4,6-triyltriimino)tribenzoat (Uvinul®T150)
Broadband filters such as for example:
  2-ethyl hexyl-2-cyano-3,3-diphenyl acrylate (Neo Heliopan®303)
  ethyl-2-cyano-3,3'-diphenyl acrylate
  2-hydroxy-4-methoxy benzophenone (Neo Heliopan®BB)
  2-hydroxy-4-methoxy benzophenone-5-sulfonic acid
  dihydroxy-4-methoxy benzophenone 2,4-dihydroxy benzophenone
tetrahydroxy benzophenone
2,2'-dihydroxy-4,4'-dimethoxy benzophenone
2-hydroxy-4-n-octoxy enzophenone
2-hydroxy-4-methoxy-4'-methyl benzophenone
sodium hydroxylmethoxy benzophenone sulfonate
disodium-2,2'-dihydroxy-4,4'-dimethoxy-5,5'-disulfobenzophenone
phenol, -(2H-benzotriazol-2-yl)-4-methyl-6-(2-methyl-3 (1,3,3,3-tetramethyl-1-(trimethylsilyl)-oxy)-disiloxanyl)-propyl), (Mexoryl®XL)
2,2'-methylene-bis-(6-(2H-benztriazol-2-yl)-4-1,1,3,3-tetramethylbutyl)-phenol), (Tinosorb®M)
2,4-bis-[4-(2-ethyl hexyloxy)-2-hydroxyphenyl]-1,3,5-triazine
2,4-bis-[{(4-(2-Ethyl-hexyloxy)-2-hydroxyl}-phenyl]-6-(4-methoxyphenyl)-1,3,5-triazine, (Tinosorb®S)
2,4-bis-[{(4-(3-sulfonato)-2-hydroxy}-propyloxy)-2-hydroxyl-phenyl]-6-(4-methoxyphenyl)-1,3,5-triazine sodium salt
2,4-bis-[{(3-(2-propyloxy)-2-hydroxy-propyloxy)-2-hydroxyl}-phenyl]-6-(4-methoxy-phenyl)-1,3,5-triazine
2,4-bis-[{4-(2-ethyl-hexyloxy)-2-hydroxy}-phenyl]-6-[4-(2-methoxyethyl-carbonyl)-phenylamino]-1,3,5-triazine
2,4-bis-[{4-(3-(2-propyloxy)-2-hydroxy-propyloxy)-2-hydroxyl}phenyl]-6-[4-(2-ethylcarboxyl)-phenylamino]-1,3,5-triazine
2,4-bis-[{4-(2-ethyl-hexyloxy)-2-hydroxy}-phenyl]-6-(1-methyl-pyrrol-2-yl-)-1,3,5-triazine
2,4-bis-[{4-tris-(trimethylsiloxy-silylpropyloxy)-2-hydroxy}-phenyl]-6-(4-methoxyphenyl)-1,3,5-triazine
2,4-bis-[{4-(2"-methylpropenyloxy)-2-hydroxy}-phenyl]-6-(4-methoxyphenyl)-1,3,5-triazine
2,4-bis-[{4-(1',1',1',3'5',5',5'-heptamethylsiloxy-2"-methyl-propyloxy)-2-hydroxy}-phenyl]-6-(4-methoxyphenyl)-1,3,5-triazine UVA Filters Such as for Example:
4-isopropyl dibenzoyl methane
terephthalylidene-dibornan sulfonic acid and salts (Mexoryl®SX)
4-t-butyl-4'-methoxy-dibenzoyl methane (Avobenzon)/ (Neo Heliopan®357)
phenylene-bis-benzimidazyl-tetrasulfonic acid disodium salt (Neo Heliopan®AP)
2,2'-(1,4-phenylene)-bis-(1H-benzimidazol-4,6-disulfonic acid), monosodium salt
2-(4-diethylamino-2-hydroxybenzoyl)benzoic acid hexylester (Uvinul® A Plus)
Indanylidene compounds according to DE 100 55 940 (=WO 02/38537)

Here, UV absorbers particularly suitable for a combination are
p-aminobenzoic acid
3-(4'-trimethyl ammonium)-benzylidene-bornan-2-one-methyl sulfate
salicylic acid homomethyl ester (Neo Heliopan®HMS)
2-hydroxy-4-methoxy-benzophenone (Neo Heliopan®BB)
2-phenyl benzimidazol sulfonic acid (Neo Heliopan®Hydro)
terephthalylidene-dibornan sulfonic acid and salts (Mexoryl®SX)
4-tert.-butyl-4'-methoxy dibenzoyl methane (Neo Heliopan®357)
3-(4'-sulfo)benzylidene-bornan-2-one and salts
2-ethyl hexyl-2-cyano-3,3-diphenyl acrylate (Neo Heliopan®303)
N-[(2 and 4)-[2-(oxoborn-3-ylidene)methyl]benzyl]-acrylamide polymer
p-methoxy cinnamon acid-2-ethyl hexyl ester (Neo Heliopan®AV)
p-aminobenzoic acid ethyl ester (25 mole) ethoxylated
p-methoxy cinnamon acid isoamyl ester (Neo Heliopan®E1000)
2,4,6-trianilino-(p-carbo-2'-ethyl hexyl-1'-oxy)-1,3,5-triazine (Uvinul®T150)
phenol, 2-(2H-benzotriazol-2-yl)-4-methyl-6-(2-methyl-3 (1,3,3,3-tetramethyl-1-(trimethylsilyl)-oxy)-disiloxanyl)-propyl), (Mexoryl®XL)
4,4'-[(6-[4-(1,1-dimethyl)-aminocarbonyl)-phenylamino]-1,3,5-triazine-2,4-diyl)-diimino]-bis-(benzoic acid-2-ethyl hexyl ester), (UvasorbHEB)
3-(4'-methyl benzylidene)-d,l-camphor (Neo Helipan®MBC)
3-benzylidene camphor
salicylic acid-2-ethyl hexyl ester (Neo Helipan®OS)
4-dimethyl aminobenzoic acid-2-ethyl hexyl ester (Padimate O)
hydroxy-4-methoxy-benzophenone-5-sulfonic acid and Na salt
2,2'-methylene-bis-(6-(2H-benztriazol-2-yl)-4-1,1,3,3-tetramethylbutyl)-phenol), (Tinosorb® M)
phenylene-bis-benzimidazyl-tetrasulfonic acid disodium salt (Neo Heliopan®AP)
2,4-bis-[{(4-(2-ethyl-hexyloxy)-2-hydroxyl}-phenyl]-6-(4-methoxyphenyl)-1,3,5-triazine, (Tinosorb®S)
benzylidene malonate polysiloxane (Parsol®SLX)
menthyl anthranilate (Neo Heliopan®MA)
2-(4-diethylamino-2-hydroxybenzoyl)benzoic acid hexyl ester (Uvinul® A Plus)
indanylidene compounds according to DE 100 55 940 (=WO 02/38537)

Advantageous anorganic light protection pigments are finely dispersed metal oxides and metal salts, for examples titanium dioxides, zinc oxide (ZnO), iron oxides (e.g. $Fe_2O_3$), aluminum oxide ($Al_2O_3$); cerium oxides (e.g. $Ce_2O_3$), manganese oxides (e.g. MnO), zirconium oxide ($ZrO_2$), silicon oxide ($SiO_2$), mixed oxides of the corresponding metals as well as mixtures of such oxides, barium sulfate and zinc stearate. Particularly preferably these are pigments on the basis of $TiO_2$ or zinc oxide. In preferred embodiments, the particles have an average diameter of less than 100 nm, preferably between 5 and 50 nm and particularly preferably between 15 and 30 nm. They may have a spherical shape, however, also particles having an ellipsoidal shape or a shape deviating from the spherical shape in other ways may be used. The pigments may also be present in a form in which they are surface treated, i.e. hydrophilized or hydrophobized. Typical examples include coated titanium dioxides such as for example titanium dioxide T 805 (Degussa) or Eusolex® T2000 (Merck) or coated zinc oxide such as for example zinc oxide NDM. As hydrophobic coating agents above all silicones and here especially trialkoxy octysilane or simethicone may be considered. With regard to sun protection products, so-called micro and nano pigments are preferably used. Preferably, zinc micro or nano pigments are used.

The overall amount of anorganic pigments, in particular of hydrophobic anorganic micropigments in the ready-made compositions according to the invention, is advantageously in the range of 0.1 to 30% by wt., preferably 0.1 to 10.0, in particular 0.5 to 6.0% by wt. in relation to the overall weight of the composition.

ii) Special Embodiments for Compositions According to the Invention for Application Onto Hair According to a further preferred embodiment, the compositions according to the invention are a hair care product (hair conditioning product).

Preferably, the hair care products according to the invention are present in the form of a styling foam, hair mousse, hair gel, shampoo, hair spray, hair foam, hair end fluid, equalizer for perms, hair dyeing and bleaching agent or "hot oil treatment". Depending on the area of application, the hair cosmetic compositions may be applied as (aerosol) spray, (aerosol) foam, gel, gel spray, cream, lotion or wax.

Hair sprays include here both aerosol sprays and pump sprays without propellant gas. Hair foams include both aerosol foams and pump foams without propellant gas. Hair sprays and hair foams preferably include predominantly or exclusively water soluble or water dispersible components. If the compounds used in the hair sprays and hair foams according to the invention are dispersible in water, they may be applied in the form of aqueous micro-dispersions having particle diameters of usually 1 to 350 nm, preferably 1 to 250 nm.

The hair care products according to the invention may contain alcohol, the term alcohol is to be understood to encompass all of the alcohols that are customary in cosmetics, e.g. ethanol, isopropanol, n-propanol.

Moreover, they may contain all of the styling and conditioner polymers known in the cosmetics industry, which may be used in combination with the cooling mixtures according to the invention, if very specific properties are to be achieved.

As conventional hair cosmetic polymers, for example the above-mentioned cationic, anionic, neutral, non-ionic and amphoteric polymers are suitable, to which reference is made here.

In order to achieve certain properties, the compositions according to the invention may additionally also contain conditioning substances on the basis of silicone compounds. Suitable silicone compounds include for example polyalkyl siloxanes, polyaryl siloxanes, polyaryl alkyl siloxanes, polyether siloxanes, silicone resines or dimethicon copolyols (CTFA) and aminofunctional silicone compounds such as amodimethicone (CTFA).

The hair care products according to the invention may contain blowing agents (propellants). Blowing agents are the blowing agents that are customarily used for hair sprays or aerosol foams. Preferred are mixtures of propane/butane, pentane, dimethyl ether, 1,1-difluorethane (HFC-152a), carbon dioxide, nitrogen or pressurized air.

As emulsifiers, any of the emulsifiers customarily used in hair foams may be used. Suitable emulsifiers may be non-ionic, cationic or anionic or amphoteric.

Examples of non-ionic emulsifiers (INCI nomenclature) include laureths, e.g. Laureth-4, ceteths, e.g. Cetheth-1, polyethylene glycol cetyl ether, ceteareths, e.g. Cetheareth-25, polyglycol fatty acid glycerides, hydroxylated lecithine, lactyl ester of fatty acids, alkyl polyglycoside.

Examples of cationic emulsifiers are cetyl dimethyl-2-hydroxy ethyl ammonium dihydrogen phosphate, cetyl trimonium chloride, cetyl trimmonium bromide, cocotrimonium methyl sulfate, Quaternium-1 to x (INCI).

Anionic emulsifiers may for example be selected from the group consisting of alkyl sulfates, alkyl ether sulfates, alkyl sulfonates, alkyl aryl sulfonates, alkyl succinates, alkyl sulfosuccinates, N-alkoyl sarcosinates, acyl taurates, acyl isethionates, alkyl phosphates, alkyl ether phosphates, alkyl ether carboxylates, alpha-olefin sulfonates, in particular alkaline and earth alkaline metal salts, e.g. sodium, potassium, magnesium, calcium as well as ammonium and triethanol amine salts. The alkyl ether sulfates, alkyl ether phosphates and alkyl ether carboxylates may have between 1 and 10 ethylene oxide or propylene oxide units, preferably 1 to 3 ethylene oxide units in a molecule.

The use of gel formers may be of advantage, in order to achieve specific rheological or other application-specific properties of the gels. Any of the gel formers customarily used in the cosmetics industry may be used as gel formers. These include slightly cross-linked polyacrylic acid, for example carbomer (INCI), cellulose derivatives, e.g. hydroxypropyl cellulose, hydroxyethyl cellulose, cationically modified celluloses, polysaccharides, e.g. xanthan gum, caprylic/capric triglyceride, sodium-acrylate copolymers, Polyquaternium-32 (and) Paraffinum Liquidum (INCI), sodium-acrylate copolymers (and) Paraffinum Liquidum (and) PPG-1 Trideceth-6, acrylamido propyl trimonium chloride/acrylamide copolymers, Steareth-10 alkyl ether, acrylate copolymers, Polyquaternium-37 (and) Paraffinum Liquidum (and) PPG-1 Trideceth-6, Polyquaternium 37 (and) propylene glycol dicaprate dicaprylate (and) PPG-1 Trideceth-6, Polyquaternium-7, Polyquaternium-44.

Any of the anionic, neutral, amphoteric or cationic surfactants customarily used in shampoos may be used in the hair care products according to the invention embodied as shampoo formulations.

Suitable anionic surfactants include for example alkyl sulfates, alkyl ether sulfates, alkyl sulfonates, alkyl aryl sulfonates, alkyl succinates, alkyl sulfosuccinates, N-alkoyl sarcosinates, acyl taurates, acyl isothionates, alkyl phosphates, alkyl ether phosphates, alkyl ether carboxylates, alpha-olefin sulfonates, in particular the alkaline and earth alkaline metal salts, e.g. sodium, potassium, magnesium, calcium as well as ammonium and triethanol amine salts. The alkyl ether sulfates, alkyl ether phosphates and alkyl ether carboxylates may have between 1 and 10 ethylene oxide or propylene oxide units, preferably 1 to 3 ethylene oxide units in a molecule.

Suitable are for example sodium lauryl sulfate, ammonium lauryl sulfate, sodium lauryl ether sulfate, ammonium lauryl ether sulfate, sodium lauroyl sarcosinate, sodium oleyl succinate, ammonium lauryl sulfosuccinate, sodium dodecyl benzol sulfonate, triethanolamino dodecyl benzol sulfonate.

Suitable amphoteric surfactants include for example alkyl betaine, alkylamido propyl betaine, alkyl sulfobetaine, alkyl glycinates, alkyl carboxy glycinates, alkylamphoacetates or propionates, alkyl amphodiacetates or dipropionates.

For example, cocodimethyl sulfopropyl betaine, lauryl betaine, cocamidopropyl betaine or sodium cocamphopropionate may be used.

As non-ionic surfactants, for example the reaction products of aliphatic alcohols or alkyl phenols having 6 to 20 C atoms in the alkyl chain which may be linear or branched, with ethylene oxide and/or propylene oxide, are suitable. The amount of alkylene oxide is approx. 6 to 60 moles per mole of alcohol. Also, alkyl amine oxides, mono- or dialkyl alkanol amides, fatty acid esters of polyethylene glycolene, alkyl polyglycosides or sorbitan ether ester are suitable.

Moreover, the shampoo formulations according to the invention may contain usual cationic surfactants such as for example quaternary ammonium compounds, for example cetyl trimethyl ammonium chloride.

In order to achieve certain effects, usual conditioners may be used in the shampoo formulations in combination with the active substances according to the invention.

These include for example the above-mentioned cationic polymers with the designation polyquaternium according to INCI, in particular copolymers of vinyl pyrrolidon/N-vinyl imidazolium salts (Luviquat FC, Luviquat HM, Luviquat MS, Luviquat Care), copolymers of N-vinyl pyrrolidon/dimethyl amino ethyl methacrylate, quaternized with diethyl sulfate (Luviquat D PQ 11), copolymers of N-vinyl caprolactam/N-vinyl pyrrolidon/N-vinyl imidazolium salts (Luviquat D Hold), cationic cellulose derivatives (Polyquaternium-4 and 10), acrylamide copolymers (Polyquaternium-7). Also, protein hydrolysates may be used as well as conditioning substances on the basis of silicone compounds, for example polyalkyl siloxanes, polyaryl siloxanes, polyaryl alkyl siloxanes, polyether siloxanes or silicone resins. Further suitable silicone compounds include dimethicon copolyols (CTFA) and aminofunctional silicone compounds such as amodimethicone (CTFA). Also, cationic guar derivatives such as guar hydroxylpropyl trimonium chloride (INCI) may be used.

Cooling Plasters as Skin Care Products

In the present invention, plasters which develop a cooling effect on the skin or on mucous membranes, are also regarded as skin care products. Of course it will be obvious to a person skilled in the art that corresponding plasters may also be used for purposes other than skin care. This is explicitly included in the scope of the invention.

Plasters according to the invention used as skin care products comprise a cooling mixture according to the invention. They may be designed in any desired way, for example according to the matrix system, the membrane system or the non-woven system (Drug Dev. Ind. Pharm. 14 (1988), 183-209; Drug Dev. Ind. Pharm. 13 (1987), 589-651; Drugs of Today 23 (1987), 625-646).

In its simplest form, the matrix system consists of 3 parts: the flexible backing film, the adhesive matrix containing the cooling mixture according to the invention and a peel-off film. If a non-adhesive matrix is used, an edge region of the backing film must be provided with an adhesive, in order to ensure adhesion to the skin.

By contrast, a membrane system comprises at least 5 parts: a flexible backing film, a reservoir with a dissolved or suspended cooling mixture according to the invention, a membrane for controlling the release of the active substance, an adhesive layer deposited on the membrane and a peel-off film.

In the non-woven system, the layer comprising the cooling mixture according to the invention consists of an absorbent non-woven fabric or a porous polymer which is impregnated with an active substance solution or suspension. This layer, which is firmly connected to the backing film, is covered with a peel-off film. The edge of the backing film is provided with an adhesive for application onto the skin.

In principle, all of the cooling mixtures according to the invention may be formulated in this way.

The auxiliary agents to be used are the ones that are customary for the production of plasters. Apart from the adhesive agent, as a rule a polymer having a glass temperature between −70 and −10, in particular −55 and −25° C., as well as a carrier film which is coated with this adhesive agent, and the active substance, usually emulsifiers, thickeners as well as materials for controlling the release of the active substance as well as other auxiliary agents are added.

The adhesive polymers having the above-mentioned low glass temperatures are known for example from U.S. Pat. Nos. 2,973,282 and 3,307,544. The self-adhesive strips and films should adhere to the human skin merely on contact, however, the cohesion of the adhesive layer and the adhesion thereof on the carrier film should be greater than the adhesion on the skin, so that they may be peeled off as far as possible without leaving any residues. These are as a rule copolymerisates on the basis of acrylic and methacrylic acid esters of alcohols having 2 to 12, in particular 4 to 8 carbon atoms which may have a large number of other comonomers polymerized therein, for example (meth)acrylic acid, (meth)acrylic nitrile, (meth)acrylic amide, N-tert.-butyl-(meth-)acrylic amide, vinyl esters such as vinyl acetate, propionate or butyrate, other vinyl compounds such as styrene, further butadiene. Particular emphasis is given here to butyl acrylate and 2-ethyl hexyl acrylate. The polymers may be crosslinked by adding minor amounts of comonomers having 2 or more copolymerizable double bonds, i.e. for example of diacrylates such as butane diol diacrylate, or divinyl compounds such as divinyl benzene, or by adding other crosslinkers, for example melamine formaldehyde resins. As sticky polymers, also polyisobutylenes and polyvinyl ether with different molecular masses may be used.

The particle sizes of the dispersions should be between 50 and 500 nm, in particular between 50 and 200 nm. The particle size and the degree of crosslinking may be adjusted in a known manner as a function of the polymerization conditions and the comonomers. Smaller particle sizes and a higher degree of crosslinking may result in an increase of the release of active substance.

Matrix plasters may be produced in the usual manner by dissolving or finely dispersing the active substance in a suitable polymer solution and subsequently extracting this self-adhesive mass containing the active substance into a film by using roller or doctor blade deposition methods. In some cases it may be expedient to dissolve or extremely finely disperse the active substance prior to adding it to the polymer solution in an organic solvent such as for example ethanol or acetone. In this way, an improved distribution of the active substance in the polymer may be achieved.

The plasters may also be produced in accordance with German patent application no P 38 07 283.1 by working in the cooling mixture in a finely pulverized form, e.g. bound to a carrier (particle size lower than 200, in particular lower than 50 μm) in the aqueous latex dispersion or by dispersing or dissolving it in an aqueous emulsifier solution and admixing this mixture to the aqueous latex dispersion at a temperature of 10 to 80, in particular of 30 to 70° C.

Expediently, the cooling mixture according to the invention is provided, the emulsifier and water are added and then mixed with the polymer dispersion. The cooling mixture thus obtained as a dispersion is, if required, provided with further auxiliary agents and is, as mentioned, extracted in a manner per se known into a film on a backing film and is dried. The drying temperature may here be between room temperature and 100° C., with an optimum between the targeted rapid drying and ensuring that any blistering in the film and thermal loading of the active ingredient are avoided generally being in the order of 35 to 45° C.

This process has the significant advantage that the use of organic solvents is avoided. However, in principle also any other customary production methods for matrix plasters may be considered.

The resulting films have a thickness of 10 to 800, preferably 50 to 300 μm. Film production may be carried out in a continuous or a batchwise process. The deposition process may be repeated several times, until the film has reached the desired thickness. The sticky polymer layer contains components a) and b) of the cooling mixture according to the invention in an accumulated concentration in the range of 1 to 40, in particular 5 to 25% by wt. in relation to the overall mass of the sticky polymer layer. The same concentration also applies to the reservoir liquid in the case of the membrane system (in relation to the overall mass of the reservoir liquid) and for the cooling mixture solution or dispersion used to impregnate the non-woven fabric or the porous polymer in the case of the non-woven system (in relation to the overall mass of the solution).

As emulsifiers both for the cooling mixture and also the polymers, the surfactants customarily used for this are used, such as the sodium salt of longer-chained fatty acids and the sulfuric acid semi-ester of a (if required oxyethylated) fatty alcohol as examples of anionic surfactants as well as polyethoxylated alkyl phenols and longer-chained fatty alcohols (e.g. hexadecan-(1)-ol) and glycerine partial fatty acid esters as examples of non-ionic surfactants and co-emulsifiers.

The desired viscosity of the mass ready to be extracted may be adjusted for example using polyacrylic acids or cellulose derivatives.

As additional crosslinkers which improve cohesion and thus the adhesive properties of the films, for example melamine formaldehyde resins may be used.

In order to enhance the release of the active substance, swelling agents such as polyvinyl pyrrolidone, cellulose derivatives or polyacrylates may be used, since the film can absorb more water, so that the diffusion resistance is reduced. The release of the active substances may be further improved by adding hydrophilic plasticizers such glycerine, 1,2-propanediol of the polyethylene glycols and lipophilic plasticizers such as triacetine, dibutyl phthalate or isopropyl myristate.

Matrix plasters usually provide a first order release of active substance. By using fillers which adsorb the active substance, such as aerosil, microcrystalline cellulose or lactose, an approximately zero order release will result.

The backing film which is dried onto the self-adhesive mass containing the cooling mixture, is preferably essentially impermeable both to the active substance and to the water vapor. It may consist for example of an aluminum-plastic composite film, a metalized plastic film, a plastic film which, towards the side of the active substance, is provided with a barrier layer for example of polyvinylidene chloride, or of a simple plastic film, for example a polyester film.

The plasters according to the invention, which are designed according to the membrane system, are also manufactured in the usual manner (e.g. EP 0 186 071A2, U.S. Pat. No. 4,262, 003).

The production of the plasters designed according to the non-woven system is carried out by impregnating non-woven fabrics or porous polymers attached to the backing film with a solution or a dispersion of the cooling mixture in a hydrophilic or lipophilic solvent or solvent mix. Subsequently, the impermeable peel-off film is deposited.

Combination of Active Substances

If required, the cooling mixtures according to the invention may be combined with further known active substances, in particular with those that have a comparable effect, which means they may also comprise these active substances. For example, they may be combined with known cooling compounds such as for example menthol, menthone, N-ethyl-p-menthane carboxamide (WS-3, also referred to as menthane-3-carboxylic acid-N-ethyl amide), N-2,3-trimethyl-2-isopropyl butane amide (WS-23), menthyl lactate (Frescolat® ML), menthone glycerine acetal (Frescolat® MGA), mono-menthyl succinate (Physcool®), mono-menthyl glutarate, O-menthyl-glycerine, menthyl-N,N-dimethyl succinamate, N-(4-cyano methyl phenyl)-p-menthane carboxamide N-(2-(pyridin-2-yl)ethyl)-3-p-menthane carboxamide.

The cooling mixtures according to the invention may preferably be combined with the following active cooling substances: menthol and menthol derivatives (e.g. L-menthol, D-menthol, racemic menthol, isomenthol, neoisomenthol, neomenthol) menthyl ether (e.g. (I-menthoxy)-1,2-propanediol, (I-menthoxy)-2-methyl-1,2-propanediol, I-menthyl-methyl ether), menthyl ester (e.g. menthyl formiate, menthyl acetate, menthyl isobutyrate, menthyl lactates, L-menthyl-L-lactate, L-menthyl-D-lactate, menthyl-(2-methoxy)acetate, menthyl-(2-methoxy ethoxy)acetate, menthyl pyroglutamate), N-(4-cyano methyl phenyl)-p-menthane carboxamide, N-(2-(pyridin-2-yl)ethyl)-3-p-menthane carboxamides, menthyl carbonates (e.g. menthyl propylene glycol carbonate, menthyl ethylene glycol carbonate, menthyl glycerine carbonate or mixtures thereof), the semi-esters of mentholes with a dicarboxylic acid or their derivatives (e.g. mono-menthyl succinate, mono-menthyl glutarate, mono-menthyl malonate, O-menthyl succinic acid ester-N,N-(dimethyl)amide, O-menthyl succinic acid ester amide), menthane carboxylic acid amide (e.g. menthane carboxylic acid-N-ethylamide [WS3], Nα-(menthane-carbonyl)glycine ethyl ester [WS5], menthane carboxylic acid-N-(4-cyanophenyl) amide, menthane carboxylic acid-N-(alkoxyalkyl)amide), menthone and menthone derivatives (e.g. L-menthone glycerine ketal), 2,3-dimethyl-2-(2-propyl)-butyric acid derivatives (e.g. 2,3-dimethyl-2-(2-propyl)-butyric acid-N-methyl amide [WS23]), isopulegol or its esters (I-(−)-isopulegol, I-(−)-isopulegol acetate), menthane derivatives (e.g. p-menthane-3,8-diol), N-(4-cyano methyl phenyl)-p-menthane carboxamides, N-(2-(pyridin-2-yl)ethyl)-3-p-menthane carboxamides.

Cubebol or synthetic or natural mixtures containing cubebol, pyrrolidone derivates of cycloalkyl dione derivatives (e.g. 3-methyl-2(1-pyrrolidinyl)-2-cyclopentene-1-one) or tetrahydropyrimidine-2-ones (e.g. Icilin or related compounds such as those described in WO 2004/026840).

The cooling mixtures according to the invention may particularly preferably be combined with the following active cooling substances: N-(4-cyano methyl phenyl)-p-menthane carboxamide, N-(2-(pyridin-2-yl)ethyl)-3-p-menthane carboxamides, menthyl ether (e.g. (I-menthoxy)-1,2-propanediol, (I-menthoxy)-2-methyl-1,2-propanediol), more polar menthyl esters (e.g. menthyl lactates, L-menthyl-L-lactate, L-menthyl-D-lactate, menthyl-(2-methoxy)acetate, menthyl-(2-methoxy ethoxy)acetate, menthyl pyroglutamate), menthyl carbonates (e.g. menthyl propylene glycol carbonate, menthyl ethylene glycol carbonate, menthyl glycerine carbonate), the semi-esters of menthols with a dicarboxylic acid or the derivatives thereof (e.g. mono-menthyl succinate, mono-menthyl glutarate, mono-menthyl malonate, O-menthyl succinic acid ester-N,N-(dimethyl)amide, O-menthyl succinic acid ester amide), menthane carboxylic acid amides not according to the invention (e.g. menthane carboxylic acid-N-ethylamide [WS3], Nα-(menthane carbonyl)glycine ethyl ester [WS5], menthane carboxylic acid-N-(4-cyanophenyl)amide, menthane carboxylic acid-N-(alkoxyalkyl)amide), menthone derivatives (e.g. L-menthone glycerine ketal), 2,3-dimethyl-2-(2-propyl)-butyric acid derivatives (e.g. 2,3-dimethyl-2-(2-propyl)-butyric acid-N-methyl amide), pyrrolidone derivatives of cycloalkyl dione derivatives (e.g. 3-methyl-2(1-pyrrolidinyl)-2-cyclopentene-1-one) or tetrahydropyrimidine-2-one (e.g. Icilin or related compounds such as those described in WO 2004/026840).

Anti-Irritants

Cosmetic compositions according to the invention may also contain anti-inflammatory active substances and/or active substances that alleviate reddening and/or itching. Here, any of the anti-inflammatory active substance and/or any of the active substances for alleviating reddening and/or itching may be used that are suitable or customarily used for cosmetic and/or dermatological applications. Advantageously, steroidal anti-inflammatory active substances of the corticosteroide type are used as anti-inflammatory active substances or as active substances for alleviating reddening and/or itching, such as hydrocortisone, hydrocortisone derivatives such as hydrocortisone-17-butyrat, dexamethasone, dexamethasone phosphate, methylprednisolone or cortisone, and this list may be extended by adding further steroidal anti-inflammatory agents. Also non-steroidal anti-inflammatory agents may be used. Examples to be mentioned here include oxicams such as Piroxicam or Tenoxicam; salicylates such as Aspirin, Disalcid, Solprin or Fendosal; acetic acid derivatives such as Diclofenac, Fenclofenac, Indomethacin, Sulindac, Tolmetin or Clindanac; fenamates such as Mefenamic, Meclofenamic, Flufenamic or Niflumic; propionic acid derivatives such as Ibuprofen, Naproxen, Benoxaprofen, or pyrazols such as Phenylbutazon, Oxyphenylbutazon, Febrazon or Azapropazon. Alternatively, natural anti-inflammatory substances or substances for alleviating reddening and/or itching may be used. What can be used are plant extracts, special highly effective plant extract fractions as well as active substances of high purity isolated from plant extracts. Particularly preferred are extracts, fractions and active substances from camomile, Aloe vera, Commiphora species, Rubia species, willows, willow herbs, oats, Calendula, arnica, amber, honeysuckle, rosemary, melissa, ginger, Passiflora incarnata, Hamamelis, Pueraria, Dianthus or Echinacea as well as pure substances such as Bisabolol, Apigenin, Apigenin-7-glucosid, rosemarinic acid, boswellic acid, phytosterols, glycyrrhizic acid, Glabridin, Licochalkon A, gingerols and anthranilic acid amides such as in particular avenanthramides or dianthramides. The compositions according to the invention may also contain mixtures of two or more anti-inflammatory active substances.

The amount of anti-irritants (one or more compounds) in the compositions is preferably 0.0001 to 20% by wt., particularly preferably 0.0001-10% by wt., in particular 0.001-5% by wt., in relation to the overall weight of the composition.
Antiperspirants In addition, also antiperspirant active substances (antiperspirants) may be used particularly advantageously with the compositions according to the invention. As antiperspirant active substances, predominantly aluminum salts such as aluminum chloride, aluminum chlorhydrate, nitrate, sulfate, acetate etc. are used. Moreover, however, also the use of zinc, magnesium and zirconium compounds may be advantageous. For the application in cosmetic and dermatological antiperspirants, aluminum salts and—to a somewhat lower degree—aluminum/zirconium salt combinations have essentially proven successful. What is worth mentioning apart from that are the partially neutralized and thus more skin-compatible, although not quite so effective aluminum hydroxychlorides. Apart from aluminum salts, also other substances may be considered, such as for example a) protein precipitating substances such as formaldehyde, glutaraldehyde, natural and synthetic tannins as well as trichloroacetic acid which cause a superficial closure of the perspiratory glands, b) local anasthetics (e.g. diluted solutions of e.g. Lidokain, Prilokain or mixtures of such substances), which eliminate the sympathetic supply of the perspiratory glands by blocking the peripheral nerve tracts, c) zeoliths of type X, A or Y, which besides reducing sweat secretion also have the function of adsorbing bad odors, and d) botulinus toxin (toxin of the bacteria Chlostridium botulinum) which is also used for the treatment of hyperhidrosis, an abnormally increased secretion of sweat, and the effect of which is based on an irreversible blockage of the release of the transmitter substance acetylchonine which is relevant for the secretion of sweat. Apart from that, also peptidic botulinus toxin analogs may be used in the compositions according to the invention.

Preferred sanitary articles in terms of the invention are wet wipes, sanitary towels, tampons and refreshing tissues containing a cooling mixture according to the invention. Of course, the cooling mixtures according to the invention may also be present in any of the preferred, above-described forms. Also, the sanitary articles according to the invention may contain cosmetic compositions according to the invention, in particular in the above-described preferred variants.

Another component of the invention is the use of one, two, three or more polyols selected from group A consisting of branched or unbranched alkanediols and branched or unbranched alkanetriols each having 3-12 carbon atoms for enhancing the cooling effect of 5-methyl-2-(propane-2-yl) cyclohexyl N-ethyloxamate (formula I)

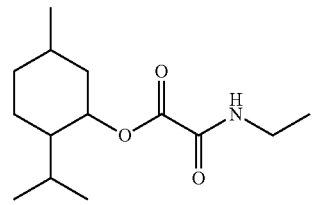

on the skin or a mucous membrane.

During this use, the cooling mixtures according to the invention will regularly develop or be used. Accordingly, it is a matter of course that the use may be carried out in connection with the preferred, above-described cooling mixtures according to the invention, the cosmetic compositions according to the invention and the sanitary articles according to the invention, in particular in their respective preferred embodiments.

A further part of the invention is a method for generating an enhanced cooling effect of 5-methyl-2-(propane-2-yl)cyclohexyl-N-ethyloxamate (formula I)

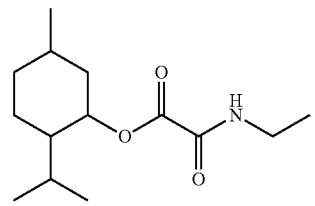 [SMILES: CCNC(=O)C(=O)OC1CC(C)CCC1C(C)C]

on the skin or a mucous membrane, comprising the following steps:
a) providing a cooling mixture or a cosmetic composition, and
b) contacting the cooling mixture or the cosmetic composition with skin or with a mucous membrane.

What is preferred in this connection is that the method is applied on human skin or a mucous membrane. However, it is also possible to use it with animals.

A further component of the invention is a method for producing a cooling mixture according to the invention or a cosmetic composition according to the invention, comprising the following steps:

a) providing 5-methyl-2-(propane-2-yl)cyclohexyl-N-ethyloxamate (formula I)

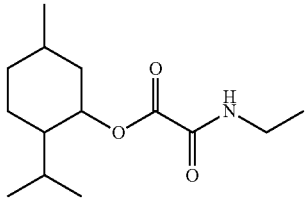 [SMILES: CCNC(=O)C(=O)OC1CC(C)CCC1C(C)C]

b) providing one, two or three polyols selected from group A consisting of branched or unbranched alkanediols and branched or unbranched alkanetriols each having 3-12 carbon atoms, and c) mixing the components provided in steps a) and b).

EXAMPLES

The invention will be illustrated in more detail below by means of examples. These examples are not intended to limit the invention. If not otherwise stated, all data refers to weight.

Application Example

In-Vivo Evaluation of a Cosmetic Composition According to the Invention

The aim of the human in vivo studies was to test the effect of the cooling mixture according to the invention in O/W formulations with regard to their cooling intensity. What was to be examined here was whether the cooling effect/cooling intensity of 5-methyl-2-(propane-2-yl)cyclohexyl-N-ethyloxamate will be enhanced in the combination of active substances according to the invention. Each individual test was carried out using 20 panellists under standardized conditions in a test institute. To this end, each test person spread two defined quantities of cream samples onto both cheeks at the same time. This half-side test allows a direct comparison of two samples, as a result of which the reproducibility of the results is markedly enhanced by comparison to a test wherein the test person has to keep cooling intensities in mind. Upon application of the samples, the test persons evaluated the cooling intensities on a scale of 1-10 within a period of 30 minutes (1=weak; 10=strong). The studies were carried out as double blind studies, therefore the test institute received the formulations in an encoded form. In order to ensure test standardization, the following conditions were selected:

- Controlled ventilation and temperature conditions in the room of the test persons
- Use of a standardized test protocol
- Detailed explanation of the test protocol
- Samples were given to the test persons in uniform, clear containers
- Samples were labeled with a three-digit code
- A sample amount of 0.3 g of cream was applied onto each cheek
- Samples were covered with a lid in order to avoid drying out of the samples
- Test persons were instructed not to use any makeup on the day of the test and not to use any cosmetic products at least two hours before the test The test persons evaluated the cooling effect of the two products on a scale of 1-10 (1=weak, 10=strong) at 32 identical points in time The data obtained during the studies was examined with regard to any significant differences between the two samples. To this end, the data was initially examined for standard normal distribution. Provided the data met the criteria of a standard normal distribution, a pairwise t test was carried out. Since the perception of the degree of coolness is different for each test person and the half-side test provides dependent data, the pairwise t test is to be used. Where no normal distribution of the values was found, significance was determined via a non-parametric Wilcoxon. The formulations had the following compositions:

TABLE 1

| | | O/W Emulsion | | |
|---|---|---|---|---|
| | Raw material (supplier) | INCI | w/w % A | w/w % B |
| A. | Emulsiphos ® (Symrise) | Potassium Cetyl Phosphate, Hydrogenated Palm Glycerides | 2.0 | 2.0 |
| | Cutina PES (Cognis) | Pentaerythrityl Distearate | 2.0 | 2.0 |
| | PCL Solid (Symrise) | Stearyl Heptanoate, Stearyl Caprylate | 2.0 | 2.0 |
| | Lanette O (Cognis) | Cetearyl Alcohol | 2.5 | 2.5 |
| | PCL Liquid 100 (Symrise) | Cetearyl ethyl hexanoate | 5.0 | 5.0 |
| | Isodragol ® | Triisononanoin | 2.0 | 2.0 |
| | Dow Corning 246 Fluid (Biesterfeld) | Cyclohexasiloxane, Cyclopentasiloxane | 2.0 | 2.0 |
| | Dragoxat ® 89 (Symrise) | Ethyl hexyl isononanoate | 3.0 | 3.0 |
| B. | Ultrez-10 (Noveon) | Carbomer | 0.2 | 0.2 |
| | Keltrol CG (CP Kelco) | Xanthan Gum | 0.15 | 0.15 |
| C. | Water | Water (Aqua) | ad 100 | ad 100 |
| | EDTA BD (BASF) | Disodium EDTA | 0.1 | 0.1 |
| | Propylene glycol (Dow) | Propylene Glycol | 2.0 | — |
| D. | Sodium Hydroxide 10% sol. | Sodium Hydroxide | 0.2 | 0.2 |
| E. | Propylene glycol (Dow) | Propylene Glycol | 3.0 | — |
| | MEO | (1R,2S,5R)-5-methyl-2-(propane-2-yl)cyclohexyl N ethyloxamate | 1.0 | 1.0 |
| | pH value | | 6.0 | 6.0 |

Information Regarding Preparation:

Phases A and C are heated separately to approx. 80° C. Phase B is dispersed in phase A.

Phase C is added to phase AB and is subsequently emulsified under an Ultra Turrax Stirrer (3 min). Subsequently, phase D is added and neutralized. The emulsion is cold-stirred using a blade mixer, with the mixing rate being reduced as the temperature decreases.

Phase E is added at 45-50° C.

BRIEF DESCRIPTION OF THE DRAWINGS

FIG. 1 is in particular used to show that MEO already has a cooling effect by itself, whereas FIG. 2 provides evidence for an increase of this cooling effect by the diol to be used according to the invention. Because of the measuring method (cheek tests with only two comparative values, respectively) two separate test series were required, which are shown up in the two separate figures.

Examples of Formulations

Formulation Example 1A

Hair Lotion

Figure 1:
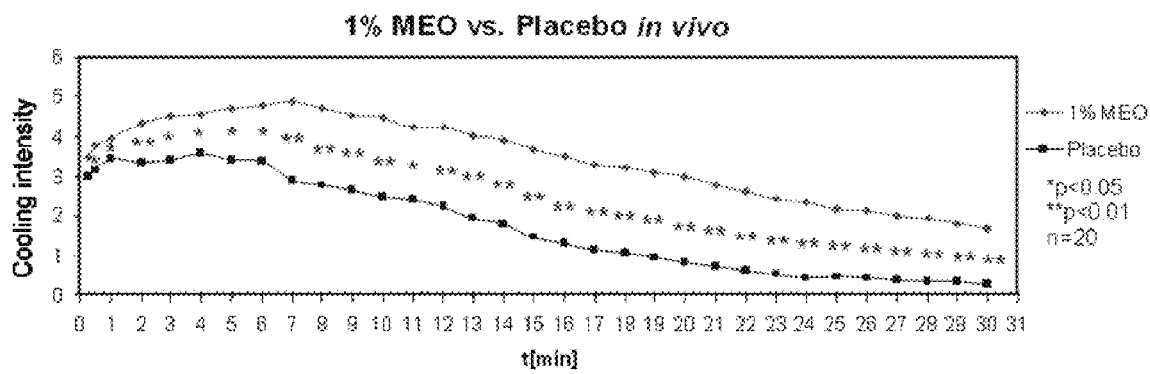
FIG. 1 shows a marked cooling effect of (1R,2S,5R)-5-methyl-2-(propane-2-yl)cyclohexyl N ethyl oxamate (MEO). The cooling effect is noticeable immediately upon application of the formulation. Moreover, the duration of the cooling effect, which is more than 30 minutes, is strongly pronounced.
Figure 2:
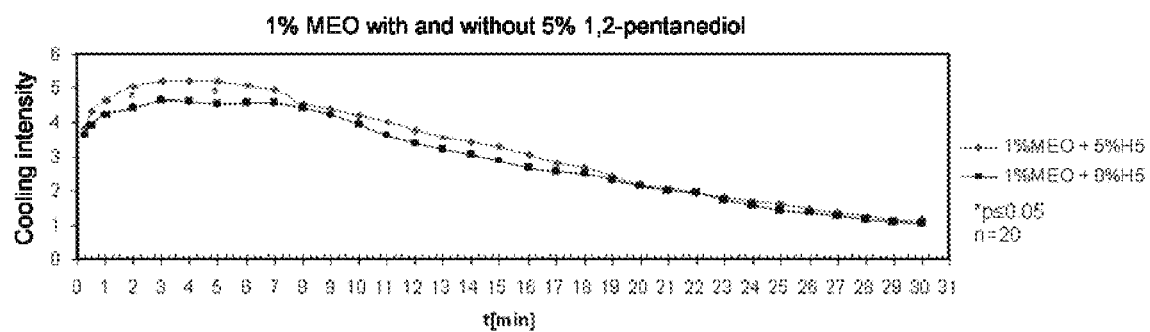
FIG. 2 shows the effect of a cooling mixture according to the invention (mixture A from Table 1), comprising (1R,2S, 5R)-5-methyl-2-(propane-2-yl)cyclohexyl_N-ethyloxamate and n-1,2-pentanediol, compared to a mixture of an identical composition, wherein the n-1,2-pentanediol was replaced with water (mixture B from Table 1). It shows that the cooling effect of the cooling mixture according to the invention, which contains pentanediol, is evaluated as being stronger throughout. After two minutes or five minutes, the increase in cooling intensity by 1,2-pentanediol is also mathematically significant. It has to be assumed that with a larger panel also further significant measurements may be generated. A corresponding increase in the effect of MEO as well as other cooling substances may also be generated by means of other diols and triols, which according to the invention may be part of group (b) of the cooling mixture according to the invention.

|   | %    | Ingredient |
|---|------|------------|
| A | q.s. | Perfume oil |
|   | 1.00 | PEG-40 Hydrogenated Castor Oil |
| B | 65.0 | alcohol |
|   | 1.0  | Panthenol |
|   | 0.5  | Polyquarternium-16 |
|   | 0.1  | Menthol |
|   | 2.00 | (1R,2S,5R)-5-methyl-2-(propane-2-yl)cyclohexyl N ethyloxamate |
|   | 3.00 | Pentylene glycol |
|   | 27.4 | Aqua dem. |

Preparation: mix phase A. Add phase B and stir until completely dissolved, adjust pH value to pH 7.0.

Formulation Example 1B

Hair Lotion

|   | %    | Ingredient |
|---|------|------------|
| A | q.s. | Perfume oil |
|   | 1.00 | PEG-40 Hydrogenated Castor Oil |
| B | 65.0 | Alcohol |
|   | 1.0  | Panthenol |
|   | 0.5  | Polyquarternium-16 |
|   | 0.1  | Menthol |
|   | 2.00 | (1R,2S,5R)-5-methyl-2-(propane-2-yl)cyclohexyl N ethyloxamate |
|   | 3.00 | Pentylene glycol |
|   | 1.00 | 4-t Butylcyclohexanol |
|   | 26.4 | Aqua dem. |

Preparation: Mix Phase A. Add phase B and stir until completely dissolved, adjust pH value to pH 7.0.

Formulation Example 2A

Hair Gel

|   | %     | Ingredient |
|---|-------|------------|
| A | 45.00 | Carbopol 940 1% in water |
|   | 0.70  | Aminomethyl Propanol |
| B | 7.50  | VP/Methacrylamide/Vinyl Imidazole Copolymer |
|   | 0.10  | Perfume oil |
|   | 0.30  | PEG-40 Hydrogenated Castor Oil |
|   | 0.30  | Preservative |
|   | 0.05  | Disodium EDTA |
|   | 0.30  | Panthenol |
|   | 8.00  | Alcohol |
|   | 5.00  | Pentylene glycol |
|   | 2.00  | (1R,2S,5R)-5-methyl-2-(propane-2-yl)cyclohexyl N ethyloxamate |
|   | 30.75 | Aqua dem. |

Preparation: Mix Phase A. Add phase B and stir until completely dissolved, adjust pH value to pH 7.0.

Formulation Example 2B

Hair Gel

|   | %     | Ingredient |
|---|-------|------------|
| A | 45.00 | Carbopol 940 1% in water |
|   | 0.70  | Aminomethyl Propanol |
| B | 7.50  | VP/Methacrylamide/Vinyl Imidazole Copolymer |
|   | 0.10  | Perfume oil |
|   | 0.30  | PEG-40 Hydrogenated Castor Oil |
|   | 0.30  | Preservative |
|   | 0.05  | Disodium EDTA |
|   | 0.30  | Panthenol |
|   | 8.00  | Alcohol |
|   | 5.00  | Pentylene glycol |
|   | 0.5   | 4-t Butylcyclohexanol |
|   | 1.50  | (1R,2S,5R)-5-methyl-2-(propane-2-yl)cyclohexyl N ethyloxamate |
|   | 30.75 | Aqua dem. |

Preparation: Mix phase A. Add phase B and stir until completely dissolved, adjust pH value to pH 7.0.

Formulation Example 3A

Cosmetic Sun Protection Composition

In the following recipes, a cosmetic sun protection composition is described that contains a combination of at least a non-organic pigment and an organic UV filter.

The formulations listed below are prepared in the usual manner as known to a person skilled in the art.

|   | %    | Ingredient |
|---|------|------------|
| A | 7.50 | Ethylhexyl cinnamic acid |
|   | 2.00 | Benzophenon-3 |
|   | 0.80 | Polyglyceryl dimer soyate |
|   | 1.00 | Sorbitane stearate |
|   | 0.50 | Tocopheryl acetate |
|   | 3.00 | Glyceryl stearate, PEG-100 Stearate |

-continued

|   | % | Ingredient |
|---|---|---|
|   | 1.00 | PEG-40 hydrogenated castor oil |
| B | 3.00 | Titanium dioxide, aluminum oxide hydrate, Dimethicon/Methicon Copolymer |
|   | 1.00 | *Butyrospermum parkii* (Shea Butter) |
|   | 6.50 | $C_{12-15}$ alkyl benzoate |
| C | 5.00 | Butylene glycol |
|   | 0.30 | Xanthan gum |
|   | 0.10 | Disodium EDTA |
|   | 0.10 | Allantoin |
| D | 1.00 | Polyacryl amide, $C_{13-14}$ isoparaffin, Laureth-7 |
|   | 5.00 | Pentylene glycol |
|   | 2.00 | (1R,2S,5R)-5-methyl-2-(propane-2-yl)cyclohexyl N ethyloxamate |
|   | 59.20 | Aqua dem. |

Formulation Example 3B

Cosmetic Sun Protection Composition

|   | % | Ingredient |
|---|---|---|
| A | 7.50 | Ethylhexyl cinnamic acid |
|   | 2.00 | Benzophenon-3 |
|   | 0.80 | Polyglyceryl dimer soyate |
|   | 1.00 | Sorbitane stearate |
|   | 0.50 | Tocopheryl acetate |
|   | 3.00 | Glyceryl stearate, PEG-100 Stearate |
|   | 1.00 | PEG-40 hydrogenated castor oil |
| B | 3.00 | Titanium dioxide, aluminum oxide hydrate, Dimethicon/Methicon Copolymer |
|   | 1.00 | *Butyrospermum parkii* (Shea Butter) |
|   | 6.50 | $C_{12-15}$ alkyl benzoate |
| C | 5.00 | Butylene glycol |
|   | 0.30 | Xanthan gum |
|   | 0.10 | Disodium EDTA |
|   | 0.10 | Allantoin |
| D | 1.00 | Polyacryl amide, $C_{13-14}$ isoparaffin, Laureth-7 |
|   | 5.00 | Pentylene glycol |
|   | 1.00 | 4-t Butylcyclohexanol |
|   | 2.00 | (1R,2S,5R)-5-methyl-2-(propane-2-yl)cyclohexyl N ethyloxamate |
|   | 60.20 | Aqua dem. |

Formulation Example 4A

Moisturizing Body Care Cream

|   | % | Ingredient |
|---|---|---|
| A | 6.0 | PEG-7 hydrogenated castor oil |
|   | 10.0 | Cetearyl ethyl hexanoate |
|   | 5.0 | Isopropyl myristate |
|   | 7.0 | Mineral oil |
|   | 0.5 | Shea Butter (*Butyrospermum parkii*) |
|   | 0.5 | Aluminum stearate |
|   | 0.5 | Magnesium stearate |
|   | 0.2 | Bisabolol |
|   | 0.7 | Quaternium-18-Hectorit |
| B | 5.0 | Dipropylene glycol |
|   | 0.7 | Magnesium sulfate |
|   | q.s. | Preservative |
|   | q.s. | Perfume oil |
|   | 4.00 | Pentylene glycol |
|   | 1.00 | (1R,2S,5R)-5-methyl-2-(propane-2-yl)cyclohexyl Nethyloxamate |
|   | 58.9 | Aqua dem. |

Preparation: Heat phases A and B separately to approx. 80° C. Mix phase B in with phase A and homogenize. Cool down to approx. 40° C. under stirring. Add phase C and homogenize again. Allow to cool down to room temperature under stirring.

Formulation Example 4B

Moisturizing Body Care Cream

|   | % | Ingredient |
|---|---|---|
| A | 6.0 | PEG-7 hydrogenated castor oil |
|   | 10.0 | Cetearyl ethyl hexanoate |
|   | 5.0 | Isopropyl myristate |
|   | 7.0 | Mineral oil |
|   | 0.5 | Shea Butter (*Butyrospermum parkii*) |
|   | 0.5 | Aluminum stearate |
|   | 0.5 | Magnesium stearate |
|   | 0.2 | Bisabolol |
|   | 0.7 | Quaternium-18-Hectorit |
| B | 5.0 | Dipropylene glycol |
|   | 0.7 | Magnesium sulfate |
|   | q.s. | Preservative |
|   | q.s. | Perfume oil |
|   | 4.00 | Pentylene glycol |
|   | 1.00 | (1R,2S,5R)-5-methyl-2-(propane-2-yl)cyclohexyl N-ethyloxamate |
|   | 0.50 | 4-t Butylcyclohexanol |
|   | 58.4 | Aqua dem. |

Preparation: Heat phases A and B separately to approx. 80° C. Mix in phase B with phase A and homogenize. Cool down to approx. 40° C. under stirring, add phase C and homogenize again. Allow to cool down to room temperature under stirring.

Formulation Example 5A

Care Shampoo

|   | % | Ingredient |
|---|---|---|
| A | 30.0 | Sodium laureth sulfate |
|   | 6.0 | Sodium cocoamphoacetate |
|   | 6.0 | Cocamidopropyl betaine |
|   | 3.0 | Sodium laureth sulfate, glycol distearate, Cocamid MEA, Laureth-10 |
|   | 7.2 | Polyquaternium-44 |
|   | 2.0 | Amodimethicon |
|   | q.s. | Perfume oil |
|   | 1.0 | Sodium chloride |
| B | 3.00 | Pentylene glycol |
|   | 1.5 | (1R,2S,5R)-5-methyl-2-(propane-2-yl)cyclohexyl N ethyloxamate |
|   | 40.3 | Aqua dem. |

Preparation: Mix and dissolve the components of phase A. Adjust pH value to 6-7 using citric acid.

Formulation Example 5B

Care Shampoo

|   | % | Ingredient |
|---|---|---|
| A | 30.0 | Sodium laureth sulfate |
|   | 6.0 | Sodium cocoamphoacetate |
|   | 6.0 | Cocamidopropyl betaine |

-continued

|   | %    | Ingredient |
|---|------|------------|
|   | 3.0  | Sodium laureth sulfate, glycol distearate, cocamid MEA, Laureth-10 |
|   | 7.2  | Polyquaternium-44 |
|   | 2.0  | Amodimethicon |
|   | q.s. | Perfume oil |
|   | 1.0  | Sodium chloride |
| B | 2.50 | Pentylene glycol |
|   | 1.5  | (1R,2S,5R)-5-methyl-2-(propane-2-yl)cyclohexyl N ethyloxamate |
|   | 0.5  | 4-t Butylcyclohexanol |
|   | 40.3 | Aqua dem. |

Preparation: Mix and dissolve the components of phase A. Adjust the pH value to 6-7 using citric acid.

Formulation Example 6A

Shower gel

|   | %    | Ingredient |
|---|------|------------|
| A | 40.0 | Sodium laureth sulfate |
|   | 5.0  | Decyl glucoside |
|   | 5.0  | Cocamidopropyl betaine |
|   | 1.0  | (1R,2S,5R)-5-methyl-2-(propane-2-yl)cyclohexyl N ethyloxamate |
|   | 1.0  | Panthenol |
|   | q.s. | Perfume oil |
|   | 3.0  | Pentylene glycol |
|   | 2.0  | Sodium chloride |
|   | 43.0 | Aqua dem. |
| B | q.s. | Citric acid |

Preparation: Mix and dissolve the components of phase A. Adjust the pH value to 6-7 using citric acid.

Formulation Example 6B

Shower Gel

|   | %    | Ingredient |
|---|------|------------|
| A | 40.0 | Sodium laureth sulfate |
|   | 5.0  | Decyl glucoside |
|   | 5.0  | Cocamidopropyl betaine |
|   | 1.0  | (1R,2S,5R)-5-methyl-2-(propane-2-yl)cyclohexyl N ethyloxamate |
|   | 1.0  | Panthenol |
|   | q.s. | Perfume oil |
|   | 3.0  | Pentylene glycol |
|   | 2.0  | Sodium chloride |
|   | 42.6 | Aqua dem. |
|   | 0.4  | 4-t Butylcyclohexanol |
| B | q.s. | Citric acid |

Preparation: Mix and dissolve the components of phase A. Adjust the pH value to 6-7 using citric acid.

Formulation Example 7A

Shampoo

|   | %    | Ingredient |
|---|------|------------|
| A | 40.0 | Sodium laureth sulfate |
|   | 5.0  | Sodium $C_{12-15}$ pareth-15 sulfonate |
|   | 5.0  | Decyl glucoside |
|   | q.s. | Perfume oil |
|   | 0.1  | Phytantriol |
|   | 40.6 | Aqua dem. |
|   | 0.5  | (1R,2S,5R)-5-methyl-2-(propane-2-yl)cyclohexyl N ethyloxamate |
|   | 0.3  | Polyquaternium-10 |
|   | 1.0  | Panthenol |
|   | q.s. | Preservative |
|   | 4.5  | Pentylene glycol |
|   | 1.0  | Laureth-3 |
|   | 2.0  | Sodium chloride |

Preparation: Mix and dissolve the components of phase A. Adjust the pH value to 6-7 using citric acid.

Formulation Example 7B

Shampoo

|   | %    | Ingredient |
|---|------|------------|
| A | 40.0 | Sodium laureth sulfate |
|   | 5.0  | Sodium $C_{12-15}$ Pareth-15 sulfonate |
|   | 5.0  | Decyl glucoside |
|   | q.s. | Perfume oil |
|   | 0.1  | Phytantriol |
|   | 40.3 | Aqua dem. |
|   | 0.5  | (1R,2S,5R)-5-methyl-2-(propane-2-yl)cyclohexyl N ethyloxamate |
|   | 0.3  | Polyquaternium-10 |
|   | 1.0  | Panthenol |
|   | q.s. | Preservative |
|   | 4.5  | Pentylene glycol |
|   | 1.0  | Laureth-3 |
|   | 0.3  | 4-t Butylcyclohexanol |
|   | 2.0  | Sodium chloride |

Preparation: Mix and dissolve the components of phase A. Adjust the pH value to 6-7 using citric acid.

Formulation Example 8A

Foot Balm

|   | %    | Ingredient |
|---|------|------------|
| A | 2.0  | Ceteareth-6, Stearyl alcohol |
|   | 2.0  | Ceteareth-25 |
|   | 5.0  | Cetearyl ethyl hexanoate |
|   | 4.0  | Cetyl alcohol |
|   | 4.0  | Glyceryl stearate |
|   | 5.0  | Mineral oil |
|   | 0.2  | Menthol |
|   | 0.5  | Camphor |
| B | 65.3 | Aqua dem. |
|   | q.s. | Preservative |

-continued

| | % | Ingredient |
|---|---|---|
| C | 1.0 | Bisabolol |
| | 1.0 | Tocopheryl acetate |
| D | 0.5 | (1R,2S,5R)-5-methyl-2-(propane-2-yl)cyclohexyl N ethyloxamate |
| | 4.5 | Pentylene glycol |
| | 5.0 | Witch hazel extract |

Preparation: Heat the components of phases A and B separately to approx. 80° C. Mix phase B in with phase A whilst homogenizing. Cool down to approx. 40° C. under stirring, add phases C and D and re-homogenize for a short time. Cool down to room temperature under stirring.

Formulation Example 8B

Foot balm

| | % | Ingredient |
|---|---|---|
| A | 2.0 | Ceteareth-6, Stearyl alcohol |
| | 2.0 | Ceteareth-25 |
| | 5.0 | Cetearyl ethyl hexanoate |
| | 4.0 | Cetyl alcohol |
| | 4.0 | Glyceryl stearate |
| | 5.0 | Mineral oil |
| | 0.2 | Menthol |
| | 0.5 | Camphor |
| B | 65.3 | Aqua dem. |
| | q.s. | Preservative |
| C | 1.0 | Bisabolol |
| | 1.0 | Tocopheryl acetate |
| D | 0.5 | (1R,2S,5R)-5-methyl-2-(propane-2-yl)cyclohexyl N ethyloxamate |
| | 4.5 | Pentylene glycol |
| | 0.3 | 4-t Butylcyclohexanol |
| | 4.7 | Witch hazel extract |

Preparation: Heat the components of phases A and B separately to approx. 80° C. Mix phase B in with phase A whilst homogenizing. Cool down to approx. 40° C. under stirring, add phases C and D and re-homogenize for a short time. Cool down to room temperature under stirring.

Formulation Example 9A

Face Cleansing Lotion—Type O/W

| | % | Ingredient |
|---|---|---|
| A | 10.0 | Cetearyl ethyl hexanoate |
| | 10.0 | Caprylic/capric triglyceride |
| | 1.5 | Cyclopentasiloxane, Cyclohexasilosane |
| | 2.0 | PEG-40 hydrogenated castor oil |
| B | 3.5 | Caprylic/capric triglyceride, sodium acrylate copolymer |
| C | 1.0 | Tocopheryl acetate |
| | 0.2 | Bisabolol |
| | q.s. | Preservative |
| | q.s. | Perfume oil |
| D | 3.0 | Polyquaternium-44 |
| | 0.5 | Cocotrimonium methosulfate |
| | 0.5 | Ceteareth-25 |
| | 2.0 | Panthenol, Propylene glycol |
| | 4.0 | Pentylene glycol |
| | 0.1 | Disodium EDTA |
| | 1.0 | (1R,2S,5R)-5-methyl-2-(propane-2-yl)cyclohexyl N ethyloxamate |
| | 60.7 | Aqua dem. |

Preparation: Dissolve phase A. Mix phase B in with phase A, work phase C into combined phases A and B. Dissolve phase D, mix into combined phases A, B and C and homogenize. Keep stirring for another 15 min.

Formulation Example 9B

Face cleansing Lotion—Type O/W

| | % | Ingredient |
|---|---|---|
| A | 10.0 | Cetearyl ethyl hexanoate |
| | 10.0 | Caprylic/capric triglyceride |
| | 1.5 | Cyclopentasiloxane, Cyclohexasilosane |
| | 2.0 | PEG-40 hydrogenated castor oil |
| B | 3.5 | Caprylic/capric triglyceride, sodium acrylate copolymer |
| C | 1.0 | Tocopheryl acetate |
| | 0.2 | Bisabolol |
| | q.s. | Preservative |
| | q.s. | Perfume oil |
| D | 3.0 | Polyquaternium-44 |
| | 0.5 | Cocotrimonium methosulfate |
| | 0.5 | Ceteareth-25 |
| | 2.0 | Panthenol, Propylene glycol |
| | 4.0 | Pentylene glycol |
| | 0.1 | Disodium EDTA |
| | 1.0 | (1R,2S,5R)-5-methyl-2-(propane-2-yl)cyclohexyl N ethyloxamate |
| | 1.0 | 4-t-Butylcyclohexanol |
| | 59.7 | Aqua dem. |

Preparation: Dissolve phase A. Mix phase B in with phase A, work phase C into combined phases A and B. Dissolve phase D, mix into combined phases A, B and C and homogenize. Keep stirring for another 15 min.

Formulation Example 10A

Body Spray

| | % | Ingredient |
|---|---|---|
| A | 3.0 | Ethyl hexyl methoxy cinnamate |
| | 2.0 | Diethylamino hydroxybenzoyl hexyl benzoate |
| | 1.0 | Polyquaternium-44 |
| | 3.0 | Pentylene glycol |
| | 2.0 | Panthenol, Propylene glycol |
| | 1.0 | Cyclopentasiloxane, Cyclohexasilosane |
| | 10.0 | Octyldodecanol |
| | 0.5 | PVP |
| | 10.0 | Caprylic/capric triglyceride |
| | 3.0 | $C_{12-15}$ alkyl benzoate |
| | 3.0 | Glycerine |
| | 1.0 | Tocopheryl acetate |
| | 0.3 | Bisabolol |
| | 0.5 | (1R,2S,5R)-5-methyl-2-(propane-2-yl)cyclohexyl N ethyloxamate |
| | 59.7 | Alcohol |

Preparation: Weigh the components of phase A and dissolve clearly.

Formulation Example 10B

Body Spray

|   | %    | Ingredient |
|---|------|------------|
| A | 3.0  | Ethyl hexyl methoxy cinnamate |
|   | 2.0  | Diethylamino hydroxybenzoyl hexyl benzoate |
|   | 1.0  | Polyquaternium-44 |
|   | 3.0  | Pentylene glycol |
|   | 2.0  | Panthenol, Propylene glycol |
|   | 1.0  | Cyclopentasiloxane, Cyclohexasiloxane |
|   | 10.0 | Octyldodecanol |
|   | 0.5  | PVP |
|   | 10.0 | Caprylic/capric triglyceride |
|   | 3.0  | $C_{12-15}$ alkyl benzoate |
|   | 3.0  | Glycerine |
|   | 1.0  | Tocopheryl acetate |
|   | 0.3  | Bisabolol |
|   | 0.5  | (1R,2S,5R)-5-methyl-2-(propane-2-yl)cyclohexyl N ethyloxamate |
|   | 0.5  | 4-t-Butylcyclohexanol |
|   | 59.2 | Alcohol |

Preparation: Weigh the components of phase A and dissolve clearly.

Formulation Example 11A

Skin Care Gel

|   | %    | Ingredient |
|---|------|------------|
| A | 3.6  | PEG-40 hydrogenated castor oil |
|   | 15.0 | Alcohol |
|   | 0.1  | Bisabolol |
|   | 0.5  | Tocopheryl acetate |
|   | q.s. | Perfume oil |
| B | 3.0  | Panthenol |
|   | 0.6  | Carbomer |
|   | 4.0  | Pentylene glycol |
|   | 0.5  | (1R,2S,5R)-5-methyl-2-(propane-2-yl)cyclohexyl N ethyloxamate |
|   | 71.9 | Aqua dem. |
| C | 0.8  | Triethanolamine |

Formulation Example 11B

Skin Care Gel

|   | %    | Ingredient |
|---|------|------------|
| A | 3.6  | PEG-40 hydrogenated castor oil |
|   | 15.0 | Alcohol |
|   | 0.1  | Bisabolol |
|   | 0.5  | Tocopheryl acetate |
|   | q.s. | Perfume oil |
| B | 3.0  | Panthenol |
|   | 0.6  | Carbomer |
|   | 4.0  | Pentylene glycol |
|   | 0.5  | (1R,2S,5R)-5-methyl-2-(propane-2-yl)cyclohexyl N ethyloxamate |
|   | 71.7 | Aqua dem. |
|   | 0.2  | 4-t Butylcyclohexanol |
| C | 0.8  | Triethanolamine |

Formulation Example 12A

After Shave Lotion

|   | %    | Ingredient |
|---|------|------------|
| A | 10.0 | Cetearyl ethyl hexanoate |
|   | 5.0  | Tocopheryl acetate |
|   | 1.0  | Bisabolol |
|   | 0.1  | Perfume oil |
|   | 0.3  | Acrylate/$C_{10-30}$ alkylacrylate crosspolymer |
| B | 15.0 | Alcohol |
|   | 1.0  | Panthenol |
|   | 3.0  | Glycerine |
|   | 1.0  | (1R,2S,5R)-5-methyl-2-(propane-2-yl)cyclohexyl N ethyloxamate |
|   | 4.0  | Pentylene glycol |
|   | 0.1  | Triethanolamine |
|   | 59.5 | Aqua dem. |

Preparation: Mix the components of phase A. Dissolve phase B, work into phase A and homogenize.

Formulation Example 12B

After Shave Lotion

|   | %    | Ingredient |
|---|------|------------|
| A | 10.0 | Cetearyl ethyl hexanoate |
|   | 5.0  | Tocopheryl acetate |
|   | 1.0  | Bisabolol |
|   | 0.1  | Perfume oil |
|   | 0.3  | Acrylate/$C_{10-30}$ alkylacrylate crosspolymer |
| B | 15.0 | Alcohol |
|   | 1.0  | Panthenol |
|   | 3.0  | Glycerine |
|   | 1.0  | (1R,2S,5R)-5-methyl-2-(propane-2-yl)cyclohexyl N ethyloxamate |
|   | 4.0  | Pentylene glycol |
|   | 0.1  | Triethanolamine |
|   | 0.6  | 4-t-Butylcyclohexanol |
|   | 58.9 | Aqua dem. |

Preparation: Mix the components of phase A. Dissolve phase B, work into phase A and homogenize.

Formulation Example 13A

After Sun Lotion

|   | %    | Ingredient |
|---|------|------------|
| A | 0.4  | Acrylate/C10-30 alkylacrylate crosspolymer |
|   | 15.0 | Cetearylethyl hexanoate |
|   | 0.2  | Bisabolol |
|   | 1.0  | Tocopheryl acetate |
|   | q.s. | Perfume oil |
| B | 1.0  | Panthenol |
|   | 15.0 | Alcohol |
|   | 3.0  | Glycerine |
|   | 1.5  | (1R,2S,5R)-5-methyl-2-(propane-2-yl)cyclohexyl N ethyloxamate |
|   | 4.0  | Pentylene glycol |
|   | 58.7 | Aqua dem. |
| C | 0.2  | Triethanolamine |

Preparation: Mix the components of phase A. Mix phase B into phase A under homogenization. Neutralize with phase C and homogenize again.

Formulation Example 13B

After Sun Lotion

|   | % | Ingredient |
|---|---|---|
| A | 0.4 | Acrylate/C10-30 alkylacrylate crosspolymer |
|   | 15.0 | Cetearylethyl hexanoate |
|   | 0.2 | Bisabolol |
|   | 1.0 | Tocopheryl acetate |
|   | q.s. | Perfume oil |
| B | 1.0 | Panthenol |
|   | 15.0 | Alcohol |
|   | 3.0 | Glycerine |
|   | 1.5 | (1R,2S,5R)-5-methyl-2-(propane-2-yl)cyclohexyl N ethyloxamate |
|   | 4.0 | Pentylene glycol |
|   | 2.0 | 4-t-Butylcyclohexanol |
|   | 56.7 | Aqua dem. |
| C | 0.2 | Triethanolamine |

Preparation: Mix the components of phase A. Mix phase B into phase A under homogenization. Neutralize with phase C and homogenize again.

Formulation Example 14A

Sun Lotion

|   | % | Ingredient |
|---|---|---|
| A | 4.5 | Ethyl hexyl methoxy cinnamic acid |
|   | 2.0 | Diethylamino hydroxybenzoyl hexyl benzoate |
|   | 3.0 | Octocrylene |
|   | 2.5 | Di-C12-13 alkylmalate |
|   | 0.5 | Tocopheryl acetate |
|   | 4.0 | Polyglyceryl-3-methyl glucose distearate |
| B | 3.5 | Cetearyl isononanoate |
|   | 1.0 | VP/Eicosene copolymer |
|   | 5.0 | Isohexadecane |
|   | 2.5 | Di-C12-13 alkylmalate |
|   | 3.0 | Titanium dioxide, Trimethoxy caprylyl silane |
| C | 5.0 | Glycerine |
|   | 1.0 | Sodium cetearyl sulfate |
|   | 0.5 | Xanthan gum |
|   | 55.7 | Aqua dem. |

-continued

|   | % | Ingredient |
|---|---|---|
| D | 1.0 | (1R,2S,5R)-5-methyl-2-(propane-2-yl)cyclohexyl N ethyloxamate |
|   | 4.0 | Pentylene glycol |
|   | 1.0 | Phenoxy ethanol, methyl paraben, ethyl paraben, butyl paraben, propyl paraben, isobutyl paraben |
|   | 0.3 | Bisabolol |

Preparation: Heat the components of phases A and B separately to approx. 80° C. Mix phase B in with phase A and homogenize. Heat phase C to approx. 80° C. into combined phases A and B under homogenization. Cool down to approx. 40° C. under stirring, add phase D and homogenize again.

Formulation Example 14B

Sun Lotion

|   | % | Ingredient |
|---|---|---|
| A | 4.5 | Ethyl hexyl methoxy cinnamic acid |
|   | 2.0 | Diethylamino hydroxybenzoyl hexyl benzoate |
|   | 3.0 | Octocrylene |
|   | 2.5 | Di-C12-13 alkylmalate |
|   | 0.5 | Tocopheryl acetate |
|   | 4.0 | Polyglyceryl-3-methyl glucose distearate |
| B | 3.5 | Cetearyl isononanoate |
|   | 1.0 | VP/Eicosene copolymer |
|   | 5.0 | Isohexadecane |
|   | 2.5 | Di-C12-13 alkyl malate |
|   | 3.0 | Titanium dioxide, trimethoxy caprylyl silane |
| C | 5.0 | Glycerine |
|   | 1.0 | Sodium cetearyl sulfate |
|   | 0.5 | Xanthan gum |
|   | 55.4 | Aqua dem. |
| D | 1.0 | (1R,2S,5R)-5-methyl-2-(propane-2-yl)cyclohexyl N ethyloxamate |
|   | 4.0 | Pentylene glycol |
|   | 0.3 | 4-t-Butylcyclohexanol |
|   | 1.0 | Phenoxy ethanol, methyl paraben, ethyl paraben, butyl paraben, propyl paraben, isobutyl paraben |
|   | 0.3 | Bisabolol |

Preparation: Heat the components of phases A and B separately to approx. 80° C. Mix phase B in with phase A and homogenize. Heat phase C to approx. 80° C. into combined phases A and B under homogenization. Cool down to approx. 40° C. under stirring, add phase D and homogenize again.

The following examples illustrate possibilities for using the cooling substances according to the invention in cosmetic formulations, by the use of which a particularly pleasant cool feel on the skin and a balming of the skin may be achieved.

| Ingredient | INCI-Name | % w/w Formulation example | | | | | | | |
|---|---|---|---|---|---|---|---|---|---|
|   |   | 15 | 16 | 17 | 18 | 19 | 20 | 21 | 22 |
| (1R,2S,5R)-5-methyl-2-(propane-2-yl)cyclohexyl N ethyloxamate |   | 0.5 | 0.5 | 0.5 | 0.5 | 0.5 | 0.5 | 0.5 | 0.5 |
| SymSitive 1609 | Trans-4-tert. butyl cyclohexanol Pentylene Glycol | 1 | 1 | 1 | 1 | 1 | 1 | 1 | 1 |
| Allantoin | Allantoin |   |   |   | 0.1 |   |   |   |   |
| (−) alpha Bisabolol natural | Bisabolol | 0.1 |   |   |   |   |   |   |   |
| Abil 350 | Dimethicone |   |   | 3.0 |   |   |   |   | 2.0 |

| Ingredient | Chemical Name | 1 | 2 | 3 | 4 | 5 | 6 | 7 | 8 |
|---|---|---|---|---|---|---|---|---|---|
| Akyposoft 100 BVC | Sodium Laureth-11 Carboxylate. Laureth-10 | 8.5 | | | | | | | |
| Aloe Vera Gel Conzentrate 10:1 | Aloe Barbadensis Leaf Juice | | | | | 1.0 | | | |
| Aluminum stearate | Aluminum Stearate | | | | | | | | |
| Arlypon F | Laureth-2 | 2.5 | | | | | | | |
| Biotive ® L-Arginine | Arginine | | | | | | | | |
| Carbopol Ultrez-10 | Carbomer | | | | | | | | 0.2 |
| Carbopol Ultrez-21 | Acrylates/C10-30 Alkylacrylate Crosspolymer | | | 0.4 | | | | | |
| Covi-Ox T-70 | Tocopherol | | | 0.1 | | | | | |
| Cutina GMS V | Glyceryl Stearate | | | | | | | | 2.0 |
| Dehyton K | Cocoamido propyl Betaine | 7.0 | | | | | | | |
| Dehyquart A CA | Cetrimonium Chloride | | | | | | | | |
| Deolite | Dimethyl Phenylpropanol Pentylene Glycol | | | | | 0.5 | 0.5 | | |
| Dow Corning 246 fluid | Cyclohexasiloxane | | | | | | 1.0 | | |
| D-Panthenol 75 L | Panthenol | | | 1.0 | | | | | |
| Dracorin ® 100 S.E.P. | Glyceryl Stearate PEG-100 Stearate | | | | | | 0.5 | | |
| Dracorin ® CE | Glyceryl Stearate/Citrate | | | | | | | | |
| Dracorin ® GOC | Glyceryl Oleate Citrate Caprylic Capric Triglyceride | | | | | | 2.0 | | |
| Drago-Beta-Glucan | Water (Aqua). Butylene Glycol. Glycerin. Avena Sativa (Oat) Kernel Extract | | | | | | | | |
| DragoCalm ® | Water. Glycerin. Avena Sativa (Oat Kernel Extract) | | | | | | | | |
| Dragocide ® Liquid | Phenoxy ethanol Methyl paraben Ethyl paraben Butyl paraben Propyl paraben Isobutyl paraben | | 0.5 | 0.8 | | | 0.8 | 0.8 | |
| Dragoderm ® | Glycerin. Triticum Vulgare (Wheat) Gluten. Water (Aqua) | | | | | | | | |
| Dragosan W/O P | Sorbitan Isostearate Hydrogenated Castor Oil. Ceresin. Beeswax (Cera Alba) | | | | | | | | |
| Dragosantol ® 100 | Bisabolol | | | 0.2 | | 0.2 | | 0.2 | |
| Dragosine ® | Carnosine | | | | | | | | |
| Dragoxat ® 89 | Ethylhexyl Isononanoate | | | | | | 1.0 | | |
| EDTA BD | Disodium EDTA | | | 0.1 | | | | | |
| Emulsiphos ® | Potassium Cetyl Phosphate Hydrogenated Palm Glycerides | | | | | | | | 2.0 |
| Ethanol 96% | Ethanol | 26 | | | 81.0 | 45.0 | | | |
| Extrapone ® Ginkgo Biloba | Propylene Glycol. Water (Aqua). Ginkgo Biloba Leaf Extract. Glucose. Lactic Acid | | 1.0 | | | | | | |
| Farnesol | Farnesol | | | | | 0.5 | | | |
| Riechstoff | Perfume | 1.0 | 1.5 | 1.0 | 10.0 | 0.5 | 0.5 | 0.4 | 0.3 |
| Frescolat ® MGA | Menthone Glycerin Acetal | | | | | | 1.0 | | |
| Frescolat ® ML | Menthyl Lactate | | 0.6 | 1.0 | | 0.3 | | 0.5 | 0.3 |

-continued

| | | | | | | | |
|---|---|---|---|---|---|---|---|
| Fruitapone ® Orange B | Propylene Glycol. Water (Aqua). Citric Acid. Citrus *Aurantium Dulcis* (Orange) Juice. Trideceth-9. Bisabolol | | | | | | 1.0 |
| Genapol LRO Liquid | Sodium Laureth Sulfate | 40.0 | | | | | |
| Glycerin 99.5% | Glycerin | | 2.5 | | | 4.0 | 2.0 |
| Hydrolite ®-5 | Pentylene Glycol | | | | | | |
| Hydroviton ®-24 | Water. Pentylene Glycol. Glycerin. Lactic Acid. Sodium Lactate. Serine. Urea. Sorbitol. Sodium Chloride. Allantoin | | | | | | |
| Iso Adipat | Diisopropyl Adipate | | | | | | |
| Isodragol ® | Triisononanoin | | | | | 1.0 | |
| Jojobaöl | *Simmondsia Chinensis* (Jojoba) Seed Oil | | 2.0 | | | | |
| Keltrol CG RD | Xanthan Gum | | | | | | 0.1 |
| Lanette O | Cetearyl Alcohol | | | | | | 3.0 |
| Mineral oil | Mineral Oil | | | | | | |
| Sodium chloride | Sodium Chloride | | | | | | |
| Sodium hydroxide 10% Lsg. | Sodium Hydroxide | 0.1 | 0.8 | | | 0.6 | 0.5 |
| Sodium stearate | Sodium Stearate | | | | 9.0 | | |
| Neo Heliopan ® 303 | Octocrylene | | | | | | 5.0 |
| Neo Heliopan ® 357 | Butylmethoxy dibenzoyl methane | | | | | | 1.1 |
| Neo Heliopan ® HMS | Homosalate | | | | | | |
| Neo Heliopan ® Hydro. 25% Lsg. Neutralised using Biotive L-Arginin | Phenyl benzimidazole Sulfonic Acid | | | | | | 3.0 |
| Neo Heliopan ® AP. 10% Lsg.. neutralized using NAOH | Disodium Phenyl Dibenzimidazole Tetrasulfonate | | | | | | 3.0 |
| Neo Heliopan ® OS | Ethylhexyl Salicylate | | | | | | 5.0 |
| Neutral oil | Caprylic/Capric Triglyceride | | | | | 3.5 | |
| Ozokerite Wax 2389 | Ozokerite | | | | | | |
| PCL-Liquid 100 | Cetearyl Ethyl hexanoate | | 3.0 | | 1.0 | | |
| Pemulen TR-2 | Acrylates/C10-30 Alkylacrylate Crosspolymer | | | | | 0.3 | |
| Polymer JR400 | Polyquaternium-10 | 0.3 | | | | | |
| Polyquart H81 | PEG-15 Coco Polyamine | | | | | | |
| Propane Butane 2.7 bar | Propane. Butane | 70.4 | | | 48 | | |
| Propylene glycol | Propylene Glycol | | | | | 36.5 | 3.0 |
| Rezal 36 GP | Aluminum Zirconium Tetrachlorohydrex GLY | | | | | 5.0 | |
| Softisan 100 | Hydrogenated Coco Glycerides | | | | | | |
| Solubilizer | PEG-40 Hydrogenated Castor Oil. Trideceth-9. Propylene Glycol. Water (Aqua) | 0.5 | | 1.0 | 1.0 | | |
| Squalan herbal | Squalane | | | | | | |
| SymAmide UDA | Undecylenamide DEA. Diethanolamine | | | | 1.0 | | |
| SymCalmin ® | Pentylene Glycol. Butylene Glycol. Hydroxy phenyl Propamidobenzoic Acid | | 0.5 | | | | |
| SymClariol ® | Decylene Glycol | 0.5 | | | 0.5 | | |
| SymDeo ® MPP | Dimethyl Phenyl butanol | 0.5 | | | | 0.5 | |
| SymDiol ® 68 | 1.2 Hexanediol. Caprylyl Glycol | | | | | | |

-continued

| Ingredient | INCI-Name | | | | | | |
|---|---|---|---|---|---|---|---|
| SymGlucan ® | Water (Aqua) Glycerin. Beta Glucan | | | | | | |
| SymMollient ® W/S | Trideceth-9. PEG-5 Isononanoate | | | 1.0 | 0.5 | | |
| SymRelief ® | Bisabolol. *Zingiber Officinale* (Ginger) Root Extract | 0.2 | 0.2 | | | | |
| SymRepair ® | Hexyl decanol. Bisabolol. Cetyl hydroxyl proline Palmitamide. Stearic Acid. *Brassica Campestris* (Rapeseed Sterols) | | | | | | |
| SymVital ® | *Aloe Barbadensis* Leaf Juice Powder. Magnesium Ascorbyl Phosphate. *Rubus Idaeus* (Raspberry) Leaf Extract | | 0.1 | | | | 0.3 |
| Triethanolamin 99% | Triethanolamine | | | | | | |
| Vitamin E Acetat | Tocopherol Acetate | | 0.5 | | | | |
| Water | Water (Aqua) | ad 100 | ad 100 | ad 100 | ad 100 | ad 100 | ad 100 |

| | | % w/w Formulation example | | | | |
|---|---|---|---|---|---|---|
| Ingredient | INCI-Name | 23 | 24 | 25 | 26 | 27 |
| (1R,2S,5R)-5-methyl-2-(propane-2-yl)cyclohexyl N ethyloxamate | | 0.5 | 0.5 | 0.5 | 0.5 | 0.5 |
| SymSitive 1609 | Trans-4-tert. butyl cyclohexanol Pentylene Glycol | 1 | 1 | 1 | 1 | 1 |
| Allantoin | Allantoin | | 0.1 | | | |
| (−) alpha Bisabolol natural | Bisabolol | | 0.2 | | 0.3 | |
| Abil 350 | Dimethicone | | | | | |
| Akyposoft 100 BVC | Sodium Laureth-11 Carboxylate. Laureth-10 | | | | | |
| *Aloe Vera* Gel Conzentrate 10:1 | *Aloe Barbadensis* Leaf Juice | | | | | |
| Aluminum stearate | Aluminum Stearate | | | | 1.2 | |
| Arlypon F | Laureth-2 | | | | | |
| Biotive ® L-Arginine | Arginine | 0.5 | | | | |
| Carbopol Ultrez-10 | Carbomer | | 0.2 | | | |
| Carbopol Ultrez-21 | Acrylates/C10-30 Alkylacrylate Crosspolymer | | | | | |
| Covi-Ox T-70 | Tocopherol | | | 0.1 | | |
| Cutina GMS V | Glyceryl Stearate | | | 2.0 | | |
| Dehyton K | Cocoamido propyl Betaine | | | | | |
| Dehyquart A CA | Cetrimonium Chloride | | | | | 4.0 |
| Deolite | Dimethyl Phenylpropanol Pentylene Glycol | | | | | |
| Dow Corning 246 fluid | Cyclohexasiloxane | | | 2.0 | | |
| D-Panthenol 75 L | Panthenol | | | 1.0 | | 1.0 |
| Dracorin ® 100 S.E.P. | Glyceryl Stearate PEG-100 Stearate | | | | | |
| Dracorin ® CE | Glyceryl Stearate/Citrate | 2.0 | | | | |
| Dracorin ® GOC | Glyceryl Oleate Citrate Caprylic Capric Triglyceride | | | 2.0 | | |
| Drago-Beta-Glucan | Water (Aqua). Butylene Glycol. Glycerin. *Avena Sativa* (Oat) Kernel Extract | | 2.0 | | | |

| | | | | | |
|---|---|---|---|---|---|
| DragoCalm ® | Water. Glycerin. Avena Sativa (Oat Kernel Extract) | | 1.0 | | |
| Dragocide ® Liquid | Phenoxy ethanol Methyl paraben Ethyl paraben Butyl paraben Propyl paraben Isobutyl paraben | | | | 0.8 | 0.8 |
| Dragoderm ® | Glycerin. Triticum Vulgare (Wheat) Gluten. Water (Aqua) | | 2.0 | 2.0 | | 2.0 |
| Dragosan W/O P | Sorbitan Isostearate Hydrogenated Castor Oil. Ceresin. Beeswax (Cera Alba) | | | | 8.0 | |
| Dragosantol ® 100 | Bisabolol | | | | | |
| Dragosine ® | Carnosine | | | 0.2 | | |
| Dragoxat ® 89 | Ethylhexyl Isononanoate | 3.0 | 4.0 | 1.0 | 5.0 | |
| EDTA BD | Disodium EDTA | 0.1 | 0.1 | | | |
| Emulsiphos ® | Potassium Cetyl Phosphate Hydrogenated Palm Glycerides | | | 2.0 | | |
| Ethanol 96% | Ethanol | | | | 65.0 | |
| Extrapone ® Ginkgo Biloba | Propylene Glycol. Water (Aqua). Ginkgo Biloba Leaf Extract. Glucose. Lactic Acid | | | | | |
| Farnesol | Farnesol | | | | | |
| Riechstoff | Perfume | 0.4 | 0.3 | 1.0 | 0.3 | 0.3 |
| Frescolat ® MGA | Menthone Glycerin Acetal | | | | | |
| Frescolat ® ML | Menthyl Lactate | | | | 0.5 | |
| Fruitapone ® Orange B | Propylene Glycol. Water (Aqua). Citric Acid. Citrus Aurantium Dulcis (Orange) Juice. Trideceth-9. Bisabolol | | | | | |
| Genapol LRO Liquid | Sodium Laureth Sulfate | | | | | |
| Glycerin 99.5% | Glycerin | | 3.0 | 4.0 | 3.0 | |
| Hydrolite ®-5 | Pentylene Glycol | 5.0 | | 5.0 | | |
| Hydroviton ®-24 | Water. Pentylene Glycol. Glycerin. Lactic Acid. Sodium Lactate. Serine. Urea. Sorbitol. Sodium Chloride. Allantoin | | 1.0 | | 2.0 | |
| Iso Adipat | Diisopropyl Adipate | | 1.0 | 5.0 | | |
| Isodragol ® | Triisononanoin | | | | | |
| Jojobaöl | Simmondsia Chinensis (Jojoba) Seed Oil | | | | 2.0 | |
| Keltrol CG RD | Xanthan Gum | 0.1 | 0.2 | | | |
| Lanette O | Cetearyl Alcohol | 2.0 | 3.0 | | | 3.5 |
| Mineral oil | Mineral Oil | | | | 8.0 | |
| Sodium chloride | Sodium Chloride | | | | 1.0 | 2.0 |
| Sodium hydroxide 10% Lsg. | Sodium Hydroxide | | | | 0.4 | |
| Sodium stearate | Sodium Stearate | | | | | |
| Neo Heliopan ® 303 | Octocrylene | 8.0 | | | | |
| Neo Heliopan ® 357 | Butylmethoxy dibenzoyl methane | 3.0 | | | | |
| Neo Heliopan ® HMS | Homosalate | 5.0 | | | | |
| Neo Heliopan ® Hydro. 25% Lsg. Neutralised using Biotive L-Arginin | Phenyl benzimidazole Sulfonic Acid | 8.0 | | | | |
| Neo Heliopan ® AP. 10% Lsg.. neutralized using NAOH | Disodium Phenyl Dibenzimidazole Tetrasulfonate | 13.3 | | | | |
| Neo Heliopan ® OS | Ethylhexyl Salicylate | | | | | |

| Trade name | INCI | | | | | |
|---|---|---|---|---|---|---|
| Neutral oil | Caprylic/Capric Triglyceride | | | 5.0 | | |
| Ozokerite Wax 2389 | Ozokerite | | | | 2.0 | |
| PCL-Liquid 100 | Cetearyl Ethyl hexanoate | | | | | |
| Pemulen TR-2 | Acrylates/C10-30 Alkylacrylate Crosspolymer | | | 0.3 | | |
| Polymer JR400 | Polyquaternium-10 | | | | | |
| Polyquart H81 | PEG-15 Coco Polyamine | | | | | 3.0 |
| Propane Butane 2.7 bar | Propane. Butane | | | | | |
| Propylene glycol | Propylene Glycol | 4.0 | | | | |
| Rezal 36 GP | Aluminum Zirconium Tetrachlorohydrex GLY | | | | | |
| Softisan 100 | Hydrogenated Coco Glycerides | 1.5 | | | | |
| Solubilizer | PEG-40 Hydrogenated Castor Oil. Trideceth-9. Propylene Glycol. Water (Aqua) | | | | | |
| Squalan herbal | Squalane | | 3.0 | | | |
| SymAmide UDA | Undecylenamide DEA. Diethanolamine | | | | | |
| SymCalmin ® | Pentylene Glycol. Butylene Glycol. Hydroxy phenyl Propamidobenzoic Acid | | 1.0 | | | |
| SymClariol ® | Decylene Glycol | | | | | |
| SymDeo ® MPP | Dimethyl Phenyl butanol | | | | | |
| SymDiol ® 68 | 1.2 Hexanediol. Caprylyl Glycol | | 1.0 | | | |
| SymGlucan ® | Water (Aqua) Glycerin. Beta Glucan | | | 1.0 | | |
| SymMollient ® W/S | Trideceth-9. PEG-5 Isononanoate | | | 0.5 | | |
| SymRelief ® | Bisabolol. *Zingiber Officinale* (Ginger) Root Extract | | | 0.2 | | |
| SymRepair ® | Hexyl decanol. Bisabolol. Cetyl hydroxyl proline Palmitamide. Stearic Acid. *Brassica Campestris* (Rapeseed Sterols) | | 2.0 | 3.0 | | |
| SymVital ® | *Aloe Barbadensis* Leaf Juice Powder. Magnesium Ascorbyl Phosphate. *Rubus Idaeus* (Raspberry) Leaf Extract | | | | | |
| Triethanolamin 99% | Triethanolamine | | 0.4 | 0.3 | | |
| Vitamin E Acetat | Tocopherol Acetate | 0.5 | | | 0.2 | |
| Water | Water (Aqua) | ad 100 | ad 100 | ad 100 | ad 100 | ad 100 |

15 = Aerosol Deo-Spray
16 = Shower gel
17 = After Shave Balm
18 = Eau de Toilette
19 = Foot spray
20 = Deo stick
21 = Deo APP Roll on Emulsion
22 = Day cream O/W. approx SPF 15
23 = Sun lotion approx. SPF 25
24 = After Sun Spray
25 = After Shave
26 = Cream W/O
27 = Hair Conditioner In all of the formulation examples, the cooling effect as perceived by the test persons was enhanced in relation to comparable formulations which did not contain any C3-C12 alkanediols and alkanetriols. Provided the corresponding formulations also contained trans-4-tert. butylcyclohexanol, the cooling effect was even further enhanced compared to formulations without this compound.

It has further been shown in practice that comparable effects are achieved if in each of these above-mentioned formulations, the proportion of 1,2-pentanediol is replaced with 1,2-hexanediol at a ratio of 5:3.

The same applies to the replacement of 1,2-pentanediol with 1,2-octanediol.

This applies analogously also to the replacement of 1,2-pentanediol with 1,2-decanediol, however, the latter is only used in an amount of one fifth of the pentanediol.

According to the present invention it is additionally to be expected that as a result of a replacement of 5-methyl-2-(propane-2-yl)cyclohexyl-N-ethyloxamate with other oxamates or other cooling substances such as for example 5-methyl-2-(propane-2-yl)cyclohexyl-N-methyl oxamate, a similar effect may be achieved.

The breadth of formulations and the diversity of the examples shows that the enhancing cooling effect may be achieved over the entire range of cosmetics. As a result, a multiplicity of additional cooling mixtures and formulations will be accessible to a person skilled in the art.

The invention claimed is:

1. A cooling mixture comprising:
   (a) 5-methyl-2-(propane-2-yl)cyclohexyl-N-ethyloxamate;

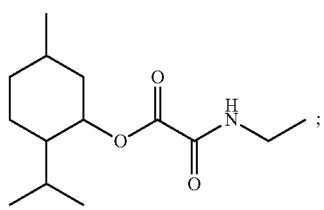
(formula I)

and
   (b) n-1,2-pentanediol
   wherein the ratio of 5-methyl-2-(propane-2-yl)cyclohexyl-N-ethyloxamate to n-1,2-pentanediol is 1:10 to 1:0.5.

2. The cooling mixture as claimed in claim 1, wherein at least part of the 5-methyl-2-(propane-2-yl)cyclohexyl-N-ethyloxamate is present in a (1R,2S,5R) configuration:

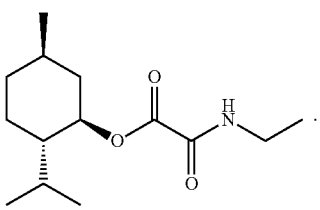
(formula II)

3. The cooling mixture as claimed in claim 2, wherein the proportion of 5-methyl-2-(propane-2-yi)cyclohexyl-N-ethyloxamate present in the (1R,2S,5R) configuration, in relation to the overall proportion of 5-methyl-2-(propane-2-yl)cyclohexyl-N-ethyloxamate, is ≥45%.

4. The cooling mixture as claimed in claim 1, further comprising trans-4-tert, butylcyclohexanol.

5. A cosmetic composition or sanitary article, comprising a cooling mixture as claimed in claim 1.

6. The cosmetic composition as claimed in claim 5, wherein the cosmetic composition is selected from the group consisting of hair care products and skin care products.

7. A method for generating an enhanced cooling effect of 5-methyl-2-(propane-2-yl)cyclohexyl-N-ethyloxamate:

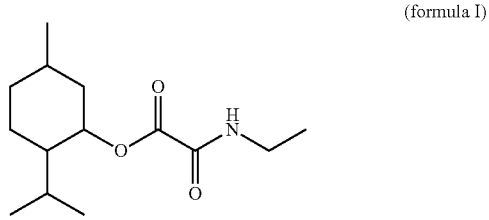 [SMILES: CCNC(=O)C(=O)OC1CC(C)CCC1C(C)C]
(formula I)

on the skin or a mucous membrane, comprising:
   a) providing a cooling mixture as claimed in claim 1; and
   b) contacting the cooling mixture with skin or a mucous membrane.

8. The method for generating a cooling mixture as claimed in claim 1, comprising:
   a) providing 5-methyl-2-(propane-2-yl)cyclohexyl-N-ethyloxamate:

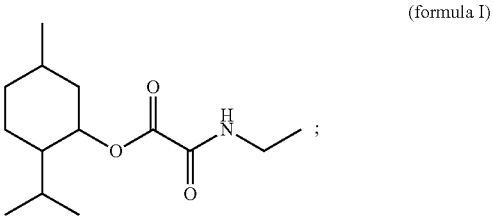 [SMILES: CCNC(=O)C(=O)OC1CC(C)CCC1C(C)C ; ";"]
(formula I)

b) providing n-1,2-pentanediol; and
   c) mixing the components provided in steps a) and b).

9. The sanitary article as claimed in claim 5, wherein the sanitary article is selected from the group consisting of sanitary towels, tampons and nappies.

10. A method for generating an enhanced cooling effect of 5-methyl-2-(propane-2-yl)cyclohexyl-N-ethyloxamate:

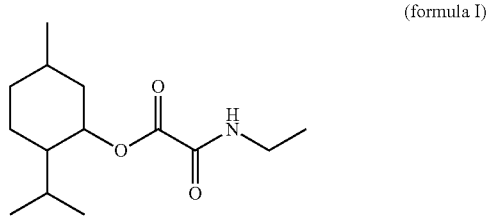 [SMILES: CCNC(=O)C(=O)OC1CC(C)CCC1C(C)C]
(formula I)

on the skin or a mucous membrane, comprising:
   a) providing a cosmetic composition as claimed in claim 6; and
   b) contacting the cosmetic composition with skin or a mucous membrane.

11. The cooling mixture as claimed in claim 2, wherein the proportion of 5-methyl-2-(propane-2-yl)cyclohexyl-N-ethyloxamate present in the (1R,2S,5R) configuration, in relation to the overall proportion of 5-methyl-2-(propane-2-yl)cyclohexyl-N-ethyloxamate, is ≥97%.

12. The cooling mixture as claimed in claim 1, wherein the ratio of 5-methyl-2-(propane-2-yl)cyclohexyl-N-ethyloxamate to the amount of n-1,2-pentanediol is 1:5 to 1:1.

* * * * *